United States Patent
Lennernäs et al.

(10) Patent No.: US 8,936,809 B2
(45) Date of Patent: Jan. 20, 2015

(54) METHOD FOR TREATING PROSTATE DISEASES BASED ON LOCAL DELIVERY OF ACTIVE SUBSTANCES

(75) Inventors: Hans Lennernäs, Uppsala (SE); Bo Lennernäs, Uddevalla (SE); Jonas Hugosson, Kungsbacka (SE); Niklas Axén, Järlåsa (SE)

(73) Assignee: Lidds AB, Helsingborg (SE)

( * ) Notice: Subject to any disclaimer, the term of this patent is extended or adjusted under 35 U.S.C. 154(b) by 1571 days.

(21) Appl. No.: 11/910,162

(22) PCT Filed: Mar. 31, 2006

(86) PCT No.: PCT/EP2006/003194
§ 371 (c)(1),
(2), (4) Date: May 8, 2008

(87) PCT Pub. No.: WO2006/103112
PCT Pub. Date: Oct. 5, 2006

(65) Prior Publication Data
US 2008/0286205 A1   Nov. 20, 2008

(30) Foreign Application Priority Data
Mar. 31, 2005   (DK) .............................. 2005 00452

(51) Int. Cl.
*A61K 9/22*     (2006.01)
*A61K 49/04*    (2006.01)
(Continued)

(52) U.S. Cl.
CPC .................................... *A61K 9/1647* (2013.01)
USPC .............. 424/468; 424/9.3; 424/9.5; 424/9.4; 424/9.1; 514/769; 514/182; 514/44 R; 514/12.1

(58) Field of Classification Search
None
See application file for complete search history.

(56) References Cited

U.S. PATENT DOCUMENTS 4,474,813 A * 10/1984 Neri et al. ...................... 514/625
5,795,330 A    8/1998 Tofighi et al.
(Continued)

FOREIGN PATENT DOCUMENTS

EP          1208850        5/2002
WO     WO 98/16209        4/1998
(Continued)

OTHER PUBLICATIONS

Rini, Brian et al., "Prostate-Specific Antigen Kinetics as a Measure of the Biologic Effect of Granulocyte-Macrophage Colony-Stimulating Factor in Patients With Serologic Progression of Prostate Cancer" Journal of Clinical Oncology, 2003, vol. 21, Issue 1, pp. 99-105.

*Primary Examiner* — Aradhana Sasan
(74) *Attorney, Agent, or Firm* — Sterne, Kessler, Goldstein & Fox P.L.L.C.

(57) ABSTRACT

A method for treating prostate related diseases in a subject, the method comprising i) optionally administering to subject an initial boost dose of one or more active substances and/or prodrugs, and ii) administering locally into the prostate a controlled release pharmaceutical composition comprising one or more active substances in a biodegradable ceramic carrier. The biodegradable hydrating ceramic may be selected from the group consisting of non-hydrated or hydrated calcium sulphate, calcium phosphate, calcium carbonate, calcium fluoride, calcium silicate, magnesium sulphate, magnesium phosphate, magnesium carbonate, magnesium fluoride, magnesium silicate, barium sulphate, barium phosphate, barium carbonate, barium fluoride, barium silicate, or mixtures thereof. In a specific embodiment, the biodegradable hydrating ceramic is non-hydrated or hydrated calcium sulphate.

40 Claims, 5 Drawing Sheets

(51) Int. Cl.
*A61K 49/00* (2006.01)
*A61K 47/00* (2006.01)
*A61K 31/56* (2006.01)
*A61K 48/00* (2006.01)
*A61K 38/00* (2006.01)
*A61K 9/16* (2006.01)

(56) References Cited

U.S. PATENT DOCUMENTS 6,497,901 B1    12/2002  Royer
6,645,974 B2 *  11/2003  Hutchinson et al. .......... 514/284
6,972,130 B1 *  12/2005  Lee et al. ...................... 424/426
2003/0147936 A1   8/2003  Sahadevan
2007/0167441 A1 * 7/2007  Halbrook et al. ........... 514/227.8

FOREIGN PATENT DOCUMENTS

| WO | WO 99/15150     | 4/1999  |
| WO | WO 99/16423     | 4/1999  |
| WO | WO 2004/084857  | 10/2004 |
| WO | WO 2004/098560  | 11/2004 |
| WO | WO 2005/039537  | 5/2005  |

* cited by examiner

METHOD FOR TREATING PROSTATE DISEASES BASED ON LOCAL DELIVERY OF ACTIVE SUBSTANCES

FIELD OF THE INVENTION

The present invention relates to a novel method of treating prostate related diseases by i) optionally administering to subject an initial burst/boost dose of one or more active substances, and ii) administering locally into the prostate a controlled release pharmaceutical composition comprising one or more active substances in a biodegradable carrier. The carrier may be a biodegradable ceramic and/or a biodegradable polymer. The carrier is suitably biocompatible. The method is suitable for treatment of e.g. prostate cancer, benign prostatic hyperplasia or acute and chronic prostatitis.

BACKGROUND OF THE INVENTION

Prostate cancer is the most common cause of non-cutaneous cancer in men and is a leading lethal malignancy with increasing incidence worldwide. The mortality rate of prostate cancer is decreasing steadily at approximately 4% yearly since 1994, while the incidence rate increases at slightly less than 2% yearly. Prostate cancer continues to have the highest incidence rate and the second highest mortality rate of any cancer for men in the US. In 2004 there were more than 230,000 new cases of prostate cancer in the US and 29,000 men died of the disease. As a group, cancer represents the second leading cause of death in men and considered alone, prostate cancer is in the top 10 overall causes of death for US men. Since the incidence of prostate cancer increases with age, the aging of the population is expected to result in an increased mortality due to prostate cancer in the future. Also, improved diagnostic techniques results in earlier diagnosis and many men are now treated while still physically and sexually active.

Current therapies for prostate cancer, including medical or surgical castration, have a significant impact on many aspects of quality of life. Non-steroidal oral antiandrogen therapy with flutamide (Eulexin™, Schering; Eulecin; Flutacan; Flutamid), bicalutamide (Casodex™, AstraZeneca) and nilutamide (Anandron™, Aventis) has demonstrated efficacy in several stages of prostate cancer and represents an alternative therapeutic strategy to castration. Survival data for men with previously untreated, locally advanced disease reveal that antiandrogen monotherapy provides survival benefits that do not differ significantly from castration. Unfortunately, systemic hormonal treatment also causes extensive side effects.

These data have stimulated research and exploration of alternative treatment methods and therapeutic agents by which current treatment regimens may be improved e.g. by local targeting as well as strategies focusing on delaying androgen independence and of influencing prostate cancer invasion. One way to provide a successful outcome of anti-androgen therapy, i.e. high efficacy and low probability for serious side effects, is to ensure local specific targeting of the therapeutic moiety at the tumor site, and thereby minimizing systemic effects.

Benign prostatic hyperplasia (BPH) can be detected histologically in more than 50% of 60 years old men and in about 90% of men 85 years old. Symptoms occur in a quarter of these men. With the current increase in the elderly population the number of cases of BPH is also increasing. According to the American Urological Association Guidelines on Management of BPH, transurethral resection of the prostate (TURP) is the most common surgical treatment for symptomatic BPH. However, the outcome is not always satisfactory for patients since hospitalization is required for TURP and there is a risk of various complications. Medical treatment, including [alpha]-1 blockers, is another possible choice for the management of BPH, but tolerance can occur in the long term. Minimally invasive therapy, positioned between medical treatment and radical surgery, has been introduced for BPH, but current methods require advanced technology and expensive devices.

The relationship between prostate inflammation and prostate cancer is increasingly becoming a focus of clinical and basic science research in urology. Reviews of epidemiologic and clinical research have suggested a link between chronic prostate inflammation and the development of prostate cancer. Evidence for the biologic plausibility of this association ranges from in vivo inflammatory models of prostate carcinogenesis to increased inflammatory mediators and markers of oxidative stress in the serum, urine, and tumors of patients with prostate cancer. Although the causal role of inflammation on prostate cancer is yet to be established, possible mechanisms include the generation of reactive oxygen species, induction of cyclooxygenase-2, and release of paracrine factors that may lead to the induction or proliferation of cancer. Prostate inflammation, particularly when associated with bacterial infection, is associated with an elevation of serum PSA levels.

The prostate is located anteriorly to the rectum. Above the prostate gland is the urinary bladder and below the urogenital diaphragm. The seminal vesicles form the ejaculatory ducts and enter the gland in a posterio-lateral direction and emerge in the urethra in approximately the middle of the gland. The gland is covered by a fibrotic capsule and has an elastic consistency. The function of the prostate gland is to secrete the milky substance of seminal fluid. Before puberty, this function does not exist and the gland is very small. Unlike many organs the growth of the prostate gland continues throughout the lifespan of a man, often resulting in a benign prostatic hyperplasia of the gland.

Pathology and Pathophysiology of Prostate Cancer

The histopathology of high-grade prostate intraepithelial neoplasia consists of architecturally benign prostate acini lined by cells that seem to be malignant. Prostates with carcinoma have more of these foci than those without carcinoma. Prostate glands with extensive high-grade prostate intraepithelial neoplasia also have more multifocal carcinomas. At the time of diagnosis a majority of patients have local prostate cancer disease without spread or metastases.

Locally advanced non-metastatic diseases include patients who have a disease penetrating through the prostate capsule or invading a seminal vesicle on digital rectal examination. The incidence of locally advanced disease varies from population to population and consists of patients who are either untouched by screening efforts or have an unusually aggressive natural history with a disease growing rapidly between screening intervals.

Androgens play an essential role in differentiation and growth of the male reproductive tract, pubertal maturation and development of secondary male sex characteristics, initiation and regulation of spermatogenesis, and male sexual behavior. Steroidal androgens increase muscle mass, bone mass, and strength; stimulate male pattern baldness; and alter serum lipid profiles and fat distribution. Testosterone, synthesized and secreted by the testes, and its more potent 5-reduced metabolite, dihydrotestosterone (DHT), are the principal biologically active endogenous androgens. Testosterone and dihydrotestosterone exert tissue-specific biological effects.

For example, testosterone functions to stimulate muscle mass, sexual development, and spermatogenesis, whereas dihydrotestosterone plays critical roles in facial and body hair growth, acne, and prostate enlargement. The actions of both testosterone and dihydrotestosterone are mediated by the intracellular androgen receptor (AR), a member of the nuclear receptor superfamily of ligand-activated transcription factors. Upon binding of testosterone or dihydrotestosterone, androgen receptor undergoes a conformational change, binds to specific DNA sequences termed androgen response elements, forms complexes with nuclear coregulatory factors, and modulates the transcription of target genes.

Androgens are important in development and treatment of prostate cancer. Withdrawal of testosterone by surgical or medical castration is a well-known treatment for prostate cancer and is effective in 75-80% of patients with metastatic prostate cancer. In animals, testosterone and dihydrotestosterone have induced prostate cancer tumors, but the link between androgens and cancer development in man is less clear.

Treatment Options

Today the treatment options for early-stage prostate cancer can be grouped into four broad categories:
- observation ("wait and see approach"),
- surgery (radical prostatectomy),
- radiotherapy (external-beam radiotherapy, brachytherapy or both),
- hormone therapy.

Especially elderly patients and those with co-morbidities may be observed without treatment. Surgery (radical prostatectomy) and radiotherapy (external-beam radiotherapy, brachytherapy or both) are the most widely accepted curative options for patients who need intervention.

Radical prostatectomy has been the standard against which other local treatments are compared. This procedure has been refined, resulting in high cure rates with decreased morbidity in appropriately selected patients. The reduction in morbidity has not resulted in reduced disease control.

External-beam radiotherapy involves daily treatment for 7-8 weeks. It has been studied extensively for early-stage prostate cancer, and like radical prostatectomy, has undergone a technological revolution, with results showing survival comparable to that of surgery, but with a different side-effect profile. Brachytherapy, which involves placement of radioactive sources directly into the prostate region of interest, is used in many centers. As a treatment for early-stage prostate cancer, it now achieves disease-free survival comparable with those of radical prostatectomy and external-beam radiotherapy. The advantage of brachytherapy is the dose escalation in the cancer without a dose escalation in the healthy tissue in the surroundings. All these local treatments have been refined, resulting in comparable cure rates; however, they all have various side-effect profiles.

Hormone therapy, although effective in the adjuvant setting for some patients with early-stage disease, can be used alone and as an alternative to observation. The prostate is a hormone-responsive organ, and this observation has been the basis for interventions for prostate cancer that either reduce serum testosterone or block the actions of this hormone.

Hormones have been used in combination with prostatectomy with limited success. However, hormones improve survival results when combined with radiotherapy, probably because of their different mechanisms of action. The hormonal therapy can independently destroy the prostate cancer and sensitize the tumor to radiation. The benefit of hormone therapy in addition to external-beam radiotherapy in intermediate-stage and locally advanced disease has been shown in many randomized studies. There seems to be particular improvement in selected patients with early-stage disease who have one or more poor prognostic factors (high-grade disease, high PSA (prostate specific antigen), or both), and if confirmed in outcome trials, hormone related therapy will probably be used much more in patients with early-stage disease in the future.

The most commonly used oral hormonal therapy today is bicalutamid (Casodex) and flutamide (Eulexin, Eulecin, Flutacan, Flutamid). The side effect spectrum of bicalutamid and flutamid, includes diarrhoea, breast enlargement, nausea, impotence, decreased libido, abdominal pain, flatulence, tiredness, asthenia, osteoporosis, sweating, hot flushes, loss of libido or erectile function, weight gain, gynaecomastia, and liver toxicity, and as a result a decreased quality of life. These side effects are to a major extent dose- and plasma/tissue concentration related, and thus dependent on high levels of the active drug in the systemic circulation and different tissues outside the prostate tissue. And, importantly, none of these side effects are related to or mediated by the local drug action in the prostate tissue. It is therefore reasonable to focus on novel therapeutic applications, which aim to improve the local concentration/amount versus time profile and increase the action of the anticancer agent in the prostate tissue.

Such an approach is valid since it has been reported that oral flutamide therapy acts via a suppression of the binding of the intraprostate dihydrotestosterone (active metabolite of testosterone) to the intracellular androgen receptor (AR).

Also many other methods for treating prostate diseases have been developed. Several are based on the intramuscular or subcutaneous application of sustained drug delivery formulations containing the active substance (such as gonadotropin hormone-releasing hormone (GnRH) agonists and GnRH antagonists). Also intraprostate (for instance antibiotics) and intralesional injection of active substances have been described. These methods have the disadvantages of producing either prolonged systemic exposure, or to require repetitive injections over substantial periods of time.

Accordingly, there is a need for developing novel methods for the treatment of prostate related diseases that lead to a more efficient treatment and at the same time make it possible to reduce the need for surgery and radio-treatments, and minimize the hormone related side-effects. To this end the present inventors have developed a method that involves local injection within the diseased prostate tissue of a controlled release composition of one or more active substances.

Such a site-specific drug delivery approach has numerous advantages in comparison to systemic pharmacological treatment methods in mammals for localized diseases. For instance, the incidence of a number of serious side effects is significantly lower and the drug will be delivered to the site of disease, i.e. the effect site, with a higher, less variable and more predictable local drug availability and effect. The daily dose that is given with a site-specific delivery composition is significantly lower than in systemic oral therapy. Hence, this site-specific drug delivery will result in reduced dose-related side effects, as the systemic concentration of the active drug(s) and its active metabolite(s) will be low, especially in comparison with corresponding oral drug therapy. It is not likely, that the low systemic concentration of the active drug will interact with other drugs in any way, i.e. no drug-drug interactions, nor any food-drug interactions are expected.

DETAILED DESCRIPTION OF THE INVENTION

Method of Treatment

Figure 1:
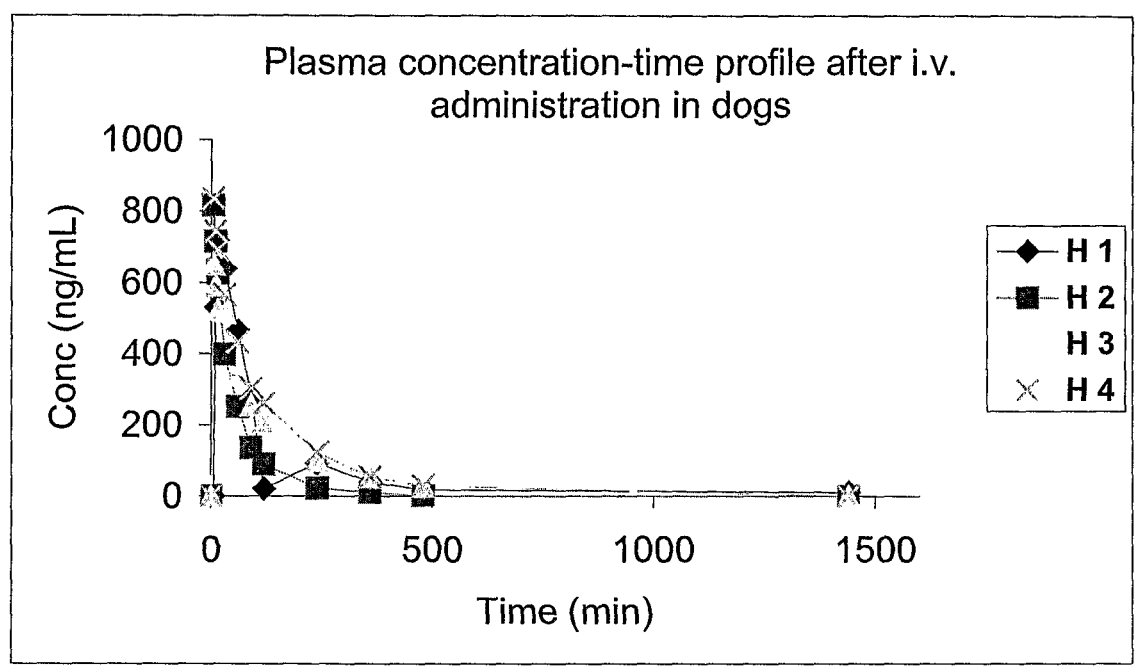
FIG. 1 is a plasma concentration-time profile after intravenous administration in dogs in accordance with an embodiment of the present invention.

The present invention relates to a method for treating prostate related diseases in a subject, the method comprising
i) optionally administering to subject an initial burst/boost dose of one or more active substances, and
ii) administering locally into the prostate a controlled release pharmaceutical composition comprising one or more active substances in a biodegradable ceramic carrier.

Normally, the subject treated is a mammal, preferably a human. The present inventors have found that a treatment involving an initial burst or boost dose of one or more active substances followed by a controlled release provided by a locally administered composition comprising the same or a different active substances may be a suitable and effective method. The boost dose ensures a proper initial concentration of a particular active substance at the site of action. The initial boost method guarantees that the least-required level of the drug in the prostate is reached immediately or within 3 hours and that the optimal steady-state concentration-effect relationship is established at once or within 3 hours (avoiding insufficient therapy from the start of the treatment period). The boost dose also helps reducing the plasma PSA (prostate specific antigen) increase caused by the local administration of the slow release formulation and it helps avoiding tolerance development. After the boost, the locally administered controlled release composition provides the prolonged delivery of the active substance(s), within the diseased prostate tissue within the local therapeutic concentration interval in the prostate tissue for each active substance. In other words, the boost dose ensures an immediate onset of the anticancer effect while the controlled release composition ensures a long lasting effect with locally sufficient concentration of the active substance(s).

Depending on the disease and condition of the subject to be treated, the boost dose and the controlled release composition may be administered simultaneously, substantially simultaneously or sequentially. As described herein, there may be situations wherein the boost dose is provided by the controlled release composition. Accordingly, the administration of i) and ii) may be separate in time, preferably by less than 24 h.

However, in a specific aspect the step of administering a boost dose is optional and may in some cases be avoided depending on the disease and e.g. any pre-treatment. Such a situation can occur e.g. in those cases where a patient is in a treatment already so that steady state concentrations are achieved and the intention is to shift the current treatment to a local controlled release treatment in the prostate tissue as described herein.

An important feature of the present invention is the administration of a controlled release pharmaceutical composition within the prostate tissue and the characteristics of such a composition. An especially suitable composition is a composition that is easy to administer to the prostate tissue without surgery, e.g. by means of injection or minimally invasive surgery, and that it remains in the prostate tissue for a prolonged period of time while releasing the active substance locally to the diseased prostate tissue. To this end, the present inventors have developed a suitable controlled release composition (see WO 2005/039537). In short, such a controlled release composition is based on a biodegradable ceramic-based matrix. The composition may be injected in liquid form (dispersion, suspension or as a paste), which may remain liquid or which may solidify to form a solid and biodegradable implant in vivo. Alternatively, it may be administered as a pre-solidified body.

An injectable, controlled release composition is designed to cure (solidify) within a time span of 5 to 20 minutes, where after the solid implant resists the movements of the surrounding tissue and the urea flow through the tissue. The solidification process is primarily governed by the amount of water contained in the composition and in the surrounding tissue upon administration as well as by the time needed for the composition to solidify. The reaction takes place with water (fluids), which is part of the solidification process, both outside and inside the body (in vivo).

According to the method of the invention the ceramic may also be implanted as solid pre-cured bodies of various shapes, e.g. cylinders, beads, rods, etc. which are small enough to be applied through cannulae, large bore needles, tubings or catheters. A human prostate may be penetrated at numerous sites, and filled with large numbers of bodies of the slow release compositions. Whether implanted as a liquid, dispersion or suspension, or a solid, the implanted solidified composition remains in the diseased tissue until the biodegradation is completed.

The method of the invention is intended for treating prostate related diseases including prostate cancer, benign prostatic hyperplasia, or acute or chronic prostatitis. The method involves administration of optionally a boost dose and a controlled release composition; at least the latter is injected into the prostate tissue or its vicinity via a transurethral, transrectal or transperineal route. The injection of the controlled release composition is made possible through clinically used standard syringes, needles, tubing systems and cannulae. The controlled release composition may also be implanted into the prostate tissue at those sites in the prostate where cancer cells or otherwise diseased tissue are present. This administration is made possible through the urethra by conventional cystoscopy or by manual guidance through the rectum by use of ultrasound imaging; magnetic resonance imaging; X-ray transmission imaging; computer tomography imaging; isotope based imaging including positron emission tomography or gamma camera/SPECT; magnetic- or radio-wave based positioning systems etc; or through the abdomen.

The boost dose, if any, may be administered by any suitable route such as, e.g., the oral, transdermal, pulmonary, nasal, sublingual, rectal or any parenteral route or it may be administered locally into the prostate tissue. Oral administration of the boost dose may be performed with already known compositions that are effective for the particular treatment. Local administration of the boost dose may be from a controlled release formulation implanted with methods similar as for the sustained release composition. The boost dose and the controlled release administration may originate from one and the same locally implanted composition. It is generally recognized that implants containing a drug substance or a combination of several compounds for prolonged release may have some fraction of the dose available for rapidly releasable content of the drug substance or the combination of several compounds on the surface of the implant. In some cases, such an amount may be sufficient to provide a local boost dose and, accordingly, in such situations a separate boost dose is not required. It is also possible to formulate a special rapidly releasable outer layer of the implant consisting of the drug substance or the combination of several compounds by applying for instance a spray technique.

Due to the inherent properties of the ceramics contained in the composition, the composition is radio-opaque and observable with standard clinical radioscopy methods, thus the positioning of controlled release composition based on a biodegradable ceramic can easily be monitored during injection and during the treatment period by e.g. ultrasound imaging; magnetic resonance imaging; X-ray transmission imaging; computer tomography imaging; isotope based imaging including positron emission tomography or gamma camera/SPECT; magnetic- or radio-wave based positioning systems. Accordingly, it is possible to ensure that the controlled release composition predominantly reaches parts of the diseased tissue and not the healthy parts of the prostate tissue. In a preferred embodiment, the method of the invention includes such a monitoring.

The radio-opaque properties of the controlled release composition can also be used to increase the accuracy of radiation treatment, thus providing the possibility of combining adjuvant/neo-adjuvant local hormone and anti-hormone treatment with high precision external beam radiotherapy with or without a brachy boost.

Monitoring with the methods mentioned above may also be employed during the treatment period. A preferred controlled release composition for use in a method according to the invention releases the active substance primarily by erosion and/or diffusion, i.e. in such a case, the degradation rate of the controlled release pharmaceutical composition is a means for in vivo monitoring the release rate of the one or more active substances. Normally, it is recommended that such a monitoring, if any, is done at predetermined intervals after the injection such as, e.g., about every 1 month, about every 2 months or about every 3 months after the first injection of the controlled release pharmaceutical composition into the prostate tissue.

As mentioned above, the controlled release pharmaceutical composition is visible in vivo in the subjects treated for monitoring and dose adjustment. Consequently, a dose of the controlled release composition may be corrected by an additional dose and the interindividual differences in degradation of the dosage form and release of the active substance may be monitored and accounted for with a higher precision rather than standardized protocol. Furthermore, during treatment the size of the prostate as well as the conditions within the prostate may change e.g. with respect to pH. Such changes may also give rise to correction of the dose or the required release of the active substance.

In the event that the monitoring reveals a faster degradation than expected or it shows a significant degradation of the controlled release pharmaceutical composition, the subject treated will normally need an additional administration of one or more supplemental doses of the one or more active substances. This dose may be a burst/boost dose of the active substance and/or a further injection in the form of a controlled release pharmaceutical composition.

The controlled release pharmaceutical composition may be designed to release the active substance during a predetermined period of time. Normally, the release period is from about 1 week to about 6 months (such as, e.g., about 1 week, about 2 weeks, about 3 weeks, about 1 month, about 2 months, about 3 months and preferably about 6 months or longer after injection of the first injected controlled release pharmaceutical composition) and, accordingly, it may be necessary in any event to repeat administration of the controlled release composition at regular intervals (i.e. if the release period is about 1 month, renewed administration may take place from about 3 weeks to about 1 month after the first administration, whereas if the release period is about 6 months, renewed administration may take place from about 5 to about 6 months after the first administration). In some cases, it may also be necessary to supplement with a boost dose depending on the physician's diagnosis and choice of treatment.

Another or an alternative method for monitoring the treatment response is by assaying PSA (prostate specific antigen) in plasma (a well-established bio-marker for prostate cancer and benign prostate hyperplasia), i.e. the same diagnostic systems used in routine practice in the management and follow-up of patients with prostate cancer. An efficient local treatment will reduce the plasma PSA level, thus reducing the risk of metastatic tissue. The effect of an efficient local treatment will also reduce the plasma and/or the tissue levels of any other biomarker for the prostate related diseases. Accordingly, in one embodiment of the invention the method further comprises a step of in vivo monitoring the release rate of the one or more active substances by monitoring the plasma levels of the one or more active substances.

In a preferred embodiment the active substance in step i) and ii) is or provides 2-hydroxy-flutamide. 2-Hydroxy-flutamide is an active metabolite of flutamide, i.e. administration of flutamide may provide an efficient therapeutic concentration of 2-hydroxy-flutamide, at least after administration orally, transdermally, pulmonary, nasal, sublingual, rectally, subcutaneously or intramuscularly.

In another specific embodiment, the active substance in step i) is flutamide and the active substance in step ii) is 2-hydroxy-flutamide.

In another preferred embodiment the active substance in step i) and ii) is bicalutamide.

For the active substances flutamide or 2-hydroxy-flutamide, the boost dose, for a normal prostate cancer patient, in step i) is in a range of from about 100 mg to about 2000 mg, such as preferably from about 500 mg to about 1000 mg per day for oral administration and in a range of from about 1 mg to about 100 mg, such as preferably from about 5 mg to about 50 mg per day for local administration in the prostate. The controlled release pharmaceutical composition in step ii) provides an amount of the active substance in a range of from about 0.1 mg to about 100 mg per day during a period of at least 1 month, 3 months, 6 months or longer.

For the active substance bicalutamide, the boost dose, for a normal prostate cancer patient, in step i) is in a range of from about 10 mg to about 1000 mg, such as preferably from about 25 mg to about 500 mg per day for oral administration and in a range of from about 1 mg to about 50 mg, such as preferably from about 5 mg to about 50 mg per day for local administration in the prostate. The controlled release pharmaceutical composition in step ii) administers an amount of the active substance in a range of from about 0.1 mg to about 100 mg per day during a period of at least 1 month, 3 months, 6 months or longer.

After oral administration of 250 mg of flutamide and/or 2-hydroxy-flutamide 3 times daily, the steady state concentration of the active metabolite in plasma, serum or blood is preferably in a range of from about 500 to about 2000 ng/ml in plasma, serum or blood. With the method of the invention, the plasma concentration of 2-hydroxy-flutamide or bicalutamide is reduced to at least 25%, such as, e.g., at least 10% or at least 5% or less of the values obtained after oral administration of a standard flutamide composition in a daily dose that provides an equivalent therapeutic effect.

When bicalutamide is used with a gonadorelin analogue in a palliative treatment the usual dose is 50 mg daily, whereas a dose of 150 mg daily may be given as monotherapy. A standard bicalutamide composition is e.g. a commercially available tablet product like Casodex® (see e.g. Martindale The Complete Drug Reference, 34$^{th}$ Edition, Pharmaceutical Press, 2005).

A standard flutamide composition is e.g. commercially available tablet or capsule product like e.g. Eulecin®, Flutacan®, Flutamid®, Eulexin® etc (see e.g. Martindale The Complete Drug Reference, 34$^{th}$ Edition, Pharmaceutical Press, 2005). The daily dose normally used in order to obtain a suitable therapeutic effect is 250 mg 3 times daily, i.e. a total daily dose of 750 mg. This dose should be efficient to obtain an effective concentration of the active moiety in the diseased prostate tissue.

The method according to the invention when involving the use of flutamide, 2-hydroxyflutamide and/or bicalutamid aims at obtaining a local concentration of 2-hydroxy-flutamide in the prostate tissue in a range of from about 0.001 nM to about 10.0 μM at steady state for a time period of from about 1 to about 6 months. The concentration of the active substance in the prostate may be estimated at steady state after administration of the first, or any supplemental, injection of the controlled release pharmaceutical composition based on the monitoring of degradation rate as mentioned above and taken the volume of the prostate and, if necessary, the plasma concentration into account. The concentration of the active substance in the prostate may also be measured by biopsy. All three drugs, flutamide, 2-hydroxyflutamide, bicalutamide, are lipophilic (hydrophobic), have low degree of hydrogen bonding and low molecular weight. Consequently, all three drugs will be rapidly and efficiently transported across the vascular space, across cell membranes and other intracellular components and provide a sufficiently high local concentration profile above the minimal antagonistic concentration.

As mentioned in the introduction the traditional treatment regimens with drugs exhibiting antiandrogen effect leads to a number of side effects. The present method involves local administration of a controlled release composition that remains on the administration site while releasing the active substance locally within the prostate tissue. Accordingly, it is possible to obtain a therapeutic effect with a much lower dosage per day and per bodyweight of the patient than that currently used by traditional oral administration or other administration routes that involves transport and distribution of the active substance by the circulatory system to the diseased prostate tissue. Furthermore, a method of the present invention provides the active substance (i.e. that of the controlled release composition) in the form of an implant, i.e. until the active substance is released it is immobilized within the biodegradable ceramic. Accordingly, the concentration of the active substance in the circulatory system is markedly reduced compared to the traditional treatments. As a consequence, all the dose-depending side effects are reduced.

Accordingly, in a specific embodiment involving use of flutamide, 2-hydroxy-flutamide and/or bicalutamide, the treatment gives a reduction in dose dependent side effects such as e.g. diarrhea, breast enlargement, nausea, impotence, decreased libido, abdominal pain, flatulence, tiredness, asthenia, osteoporosis, sweating, hot flushes, loss of libido or erectile function, weight gain, gynaecomastia, and liver toxicity compared to that obtained after oral administration of a standard flutamide or bicalutamide composition with a daily dose that provides an equivalent therapeutic effect.

The concentration of the active substance (e.g. 2-hydroxy-flutamide or flutamide or bicalutamide) in the liver tissues gives an indication of the possibility of drug induced liver specific side effects. In a specific embodiment involving the use of flutamide, 2-hydroxy-flutamide and/or bicalutamide, the local concentration of 2-hydroxy-flutamide or bicalutamide in the liver tissue is at least 5 such as, e.g., at least about 25, at least about 50, at least about 75 times or at least about 100 times less than that obtained during the absorption phase after oral administration of a standard flutamide or bicalutamide composition in a daily dose that provides an equivalent therapeutic effect. The concentration of the active substance in the liver tissue can be measured by biopsy and/or estimated from peripheral determined plasma concentrations of the active drug and the use of traditional pharmacokinetic calculation methods.

The method of the invention is well suited to be used in combination with any established treatment method or novel experimental treatment for prostate cancer, prostate hyperplasia or acute and chronic prostatitis, such as external radiation, brachy therapy, surgery or specialized diet.

The invention also relates to a kit for use according to the invention. Such a kit may contain one or more components and, optionally, instructions for use of the kit. An example of such a kit can be a first component in the form of e.g. a powder composition containing the ceramic carrier admixed with one or more active substances and, optionally, one or more pharmaceutically acceptable excipients or additives, and, as a second component water or an aqueous medium intended to be mixed with the first component before use and then administered to the subject either before or after solidification of the thus obtained composition.

Either the first or the second component may include one or more substances suitable for adjusting the release rate of the active substance(s), for improving the injectability of the composition (e.g. viscosity adjusting agents including thickening agents like cellulose or cellulose derivative) or for improveing the solidification properties of the composition. To this end, it may be substances that increase or decrease the solidification process dependent on the intended use of the composition. Further additives like e.g. stabilizers to improve the stability of the drug substance may be included (e.g. antioxidants, pH adjusting agents etc.).

In another embodiment, a kit of the invention may as a first component comprise a composition of one or more of the active substances, wherein the release of these substances after administration is intended to be relatively fast in order to ensure a suitably high local initial concentration of the active substance(s). A second component of such a kit can suitably contain a controlled release composition of one or more active substances in the form of a ceramic composition as described herein. Optionally, a third component is included in the form of water or an aqueous medium intended to be mixed with the second component before use and then administered to the subject either before or after solidification of the thus obtained composition.

Accordingly, the invention also relates to a kit comprising:
i) a first component comprising a biodegradable and hydrating ceramic carrier and one or more active substances,
ii) a second component comprising water or an aqueous medium.

Alternatively, a kit according to the invention comprises:
i) a first component comprising a biodegradable and hydrating ceramic carrier and, optionally, one or more active substances,
ii) a second component comprising water or an aqueous medium and one or more active substances.

In another embodiment a kit according to the invention comprises:
i) a first component comprising a biodegradable and hydrating ceramic carrier and, optionally, one or more active substances,
ii) a second component comprising one or more active substance,
iii) a third component comprising water or an aqueous medium and, optionally, one or more active substances.

A kit according to the invention is suitably used for the preparation of a composition for controlled release of one or more active substances.

In a specific embodiment, a kit comprises:
i) a first component giving an initial boost dose of one or more active substances and/or prodrugs; and
ii) a second component comprising a controlled release pharmaceutical composition comprising one or more active substances in a biodegradable ceramic carrier.

In such kits, the first component may be a pharmaceutical composition for local administration in the prostate, such as e.g., a injectable composition including a pharmaceutical composition comprising a ceramic carrier.

Specific embodiments are mentioned in the following. However, these examples are for illustrative purposes only and not intended to limit the invention in any way.

In a first embodiment, a kit for the treatment of prostate related diseases comprises:

First component A: A parenteral pharmaceutical formulation based on hydratable ceramics in powder form containing an active drug or a combination of active drugs in a total amount of up to 50% of the total composition, for a release duration of 3 weeks to 6 months. The ceramic may favourably be based on calcium sulphate and the active drug may favourably be an anti-androgen, e.g. 2-hydroxyflutamide; an enzymatic inhibitor, e.g. finasteride; a cytostatic agent, e.g. cyclophosphamide; an anti-inflammatory agent, e.g. an NSAID, alone or in any combination.

Second component B: A water based solution for the preparation of an injectable paste.

The formulation to be administered is prepared by mixing A with B in proportions up to 50% of water in the powder, and is positioned in the prostate gland by injection or by surgery in total amounts of up to 10 ml. The composition may solidify by hydration in vivo or ex vivo.

In a kit of this type of particular interest A contains:
250 mg of 2-hydroxyflutamide (e.g. Catalogue No. 161.01 from Micromol), mixed into a ceramic powder mix of:
2.25 g of calcium sulphate di-hydrate (e.g. Product No 12090 from Riedel-de-Haen, or Product No. 30,766-1 from Sigma-Aldrich in hydrated form) or 4.75 g of calcium sulphate di-hydrate, or a combination of:
2.25 g calcium sulphate di-hydrate and 2.5 g calcium sulphate hemi-hydrate or 5.0 g calcium sulphate hemi-hydrate.

In a kit of this type of particular interest B contains:
5.0 ml of a water solution with 1.0% of methyl cellulose (as a thickening agent) and 1.0% of acetic acid (as a curing retarder), or similar additives with similar effects of viscosity and curing time.

The methyl cellulose is suitably Product No 64632, Ph Eur from Fluka, and the acetic acid is suitably Product No 45741 from Fluka. The solution is suitably prepared from Product No 95280, Aqua Purificata, Ph Eur from Fluka.

A paste with a viscosity suitable for injection into the prostate gland is achieved by mixing 3.5 ml of the water solution with 2.5 g calcium sulphate di-hydrate and 5.0 g calcium sulphate hemi-hydrate and 250 mg of 2-hydroxyflutamide; or correspondingly for the other powder mixes.

The water solution is mixed with the powder using a spatula, and suitably transferred to a 10 ml syringe and injected to place in the prostate gland within 5 minutes after mixing (due to the curing of the paste). For the injection, a 4-6 inch long, 12-15 Gauge cannula is inserted via the rectum and the rectum wall into the prostate. Preferably each prostate lobe is penetrated individually. The positioning of the cannula and the injection of the (ultrasound opaque) paste is suitably performed using Ultra-Sound imaging. The final curing of the paste takes place in vivo.

In a second embodiment is provided a kit for the treatment of prostate related diseases, containing:
A: A parenteral pharmaceutical formulation based on calcium sulphate, in powder form containing an anti-androgen drug, e.g. 2-hydroxyflutamide, in total amounts of up to 30%, for a total release duration of 3 weeks to 6 months, during which 30-50% of the drug is released during the first 1 to 7 days and 50-70% of the drug is released after 1 week to 6 months after administration.
B: A water based solution for the preparation of A to an injectable paste.

The formulation to be administered is prepared by mixing A with B in proportions up to 50% of water in the powder, and is positioned in the prostate gland by injection or by surgery in total amounts of up to 10 ml. The composition may solidify by hydration in vivo or ex vivo.

A kit of this type of particular interest is described in the first embodiment.

A third embodiment provides a pharmaceutical formulation for the treatment of prostate related diseases. The formulation contains:
A powder of hydratable ceramics, e.g. calcium sulphate and an active drug. The active drug may favourably be an anti-androgen, e.g. 2-hydroxyflutamide; an enzymatic inhibitor, e.g. finasteride; a cytostatic agent, e.g. cyclophosphamide; an anti-inflammatory agent, e.g. an NSAID, alone or in any combination, in total amounts of up to 50%, and a water-based solution. Upon use the water solution is mixed with the powder to prepare a paste.

The water based solution may suitably contain a thickening agent such as methyl cellulose and a hydration retarder such as acetic acid.

The mixed formulation is positioned in the prostate gland and provides a total release duration of 3 weeks to 6 months of the active drug. During the release period 30-50% of the drug is released during the first 1-7 days and 50-70% of the drug is released after 1 week to 6 months after administration.

A kit of this type of particular interest is described in the first embodiment.

In a fourth embodiment, a drug releasing implant, of arbitrary shape or in particulate form, contains a hydratable ceramic, e.g. calcium sulphate and one or more active drugs, e.g. an anti-androgen such as 2-hydroxyflutamide, or a combination of active drugs.

The implant is positioned in the prostate gland and provides a total release duration of 3 weeks to 6 months of the active drug(s). During the release period 30-50% of the drug is released during the first 1-7 days and 50-70% of the drug is released after 1 week to 6 months after positioning in the prostate gland.

Implants of this type of particular interest are prepared from:
250 mg of 2-hydroxyflutamide (e.g. Catalogue No. 161.01 from Micromol)
2.25 g or 4.75 g of calcium sulphate hemi-hydrate (e.g. Product No 12090 from Riedel-de-Haen, or Product No. 30,766-1 from Sigma-Aldrich), corresponding to two relevant drug loads.
2.0 or 4.0 ml of water, suitably Product No 95280, Aqua Purificata, Ph Eur from Fluka.

From this pasty mix suitably 5 or 10 implants are moulded as e.g. rods or spheres and are made to cure before being positioned in the prostate gland through surgery.

Embodiment 5 relates to a drug releasing implant, or arbitrary shape or in particulate form, containing a hydratable ceramic, e.g. calcium sulphate and an active drug, e.g. an anti-androgen such as 2-hydroxyflutamide, or a combination of active drugs, composed of an inner hydrated core and an outer layer of ceramic.

The implant is positioned in the prostate gland and provides a total release duration of 3 weeks to 6 months of the active drug(s). During the release period 30-50% of the drug is released during the first 1-7 days and 50-70% of the drug is released after 1 week to 6 months after positioning in the prostate gland.

An implant of this type of particular interest is described in the fourth embodiment.

Embodiment 6 provides a pharmaceutical formulation containing a hydratable ceramic- based carrier in powder form (for example calcium sulphate), and an active drug. The active drug may favourably be an anti-androgen, e.g. 2-hydroxyflutamide; an enzymatic inhibitor, e.g. finasteride; a cytostatic agent, e.g. cyclophosphamide; an anti- inflammatory agent, e.g. an NSAID, alone or in any combination.

The powder is composed of two (or more) grain size fractions; one suitably <10 microns of non-hydrated grains and one in the range 50-500 microns of hydrated grains. One or both grain size fractions may be mixed with the active drug(s). The formulation further contains water, which is mixed with the powder to form a paste to be positioned in the prostate gland by injection or surgery.

In the prostate gland the formulation provides a total release duration of 3 weeks to 6 months of the active drug. During the release period 30-50% of the drug is released during the first 1-7 days and 50-70% of the drug is released after 1 week to 6 months after administration.

In a pharmaceutical formulation of this type of particular interest consists of:
250 mg of 2-hydroxyflutamide (e.g. Catalogue No. 161.01 from Micromol), embedded in 2.25 g of calcium sulphate di-hydrate (e.g. Product No 12090 from Riedel-de-Haen, or Product No. 30,766-1 from Sigma-Aldrich, in hydrated form). The powder mix of 2-hydroxyflutamide and calcium sulphate di-hydrate has a grain size suitably of 50 to 150 or 150-500 microns.
5.0 g calcium sulphate hemi-hydrate (e.g. Product No 12090 from Riedel-de-Haen, or Product No. 30,766-1 from Sigma-Aldrich).
3.5 ml of a water solution with 1.0% of methyl cellulose (as a thickening agent) and 1.0% of acetic acid (as a curing retarder), as in the first embodiment. A paste is prepared and administered as in the first embodiment.

Embodiment 7 provides a kit for treatment of prostate related diseases, containing:
A: A parenteral formulation based on hydratable ceramics in powder form containing an active drug or a combination of active drugs in a total amount of below 50% of the total composition for a release duration of 1 to 7 days. (The ceramic may favourably be based on calcium sulphate and the active drug may favourably be an anti-androgen, e.g. 2-hydroxyflutamide; an enzymatic inhibitor, e.g. finasteride; a cytostatic agent, e.g. cyclophosphamide; an anti-inflammatory agent, e.g. an NSAID, alone or in any combination.
B: A parenteral formulation based on hydratable ceramics in powder form containing an active drug or a combination of active drugs in a total amount of below 50% of the total composition for a release duration of 3 weeks to 6 months. (The ceramic may favourably be based on calcium sulphate and the active drug may favourably be an anti-androgen, e.g. 2-hydroxyflutamide; an enzymatic inhibitor, e.g. finasteride; a cytostatic agent, e.g. cyclophosphamide; an anti-inflammatory agent, e.g. an NSAID, alone or in any combination).
C: A water based solution for the preparation of A and B to an injectable paste form.

A is prepared with C and injected into the prostate gland in amounts of up to 10 ml.

B is prepared with C and injected into the prostate gland in amounts of up to 10 ml at the same occasion as A or within 7 days of the administration of A.

Embodiment 8 provides a kit for prostate cancer treatment containing:
A: An oral tablet or an injectable solution with an active drug or a combination of active drugs (such an anti-androgen, e.g. 2-hydroxyflutamide; an enzymatic inhibitor, e.g. finasteride; a cytostatic agent, e.g. cyclophosphamide; an anti-inflammatory agent, e.g. an NSAID, alone or in any combination.) for administration intravenously, subcutaneously, intra-muscularly, pulmonary, etc,—for a systemic exposure within some hours.

The component A may suitably be a 250 mg (or similar) oral tablet of 2-hydroxyflutamide, flutamide or bicalutamide, or an intravenous solution of 25 mg of 2-hydroxyflutamide, flutamide or bicalutamide dissolved in a sterile saline (54%) with polyethylene glycol (40%) and ethanol (6%).
B: A parenteral formulation based on hydratable ceramics in powder form containing an active drug or a combination of active drugs in a total amount of below 50% of the total composition for a release duration of 3 weeks to 6 months. (The ceramic may favourably be based on calcium sulphate and the active drug may favourably be an anti-androgen, e.g. 2-hydroxyflutamide; an enzymatic inhibitor, e.g. finasteride; a cytostatic agent, e.g. cyclophosphamide; an anti-inflammatory agent, e.g. an NSAID, alone or in any combination.)
C: A water based solution for the preparation of B to a paste
B and C are suitably prepared as in the first embodiment.

B is prepared with C and injected into the prostate gland in amounts of up to 10 ml at the same occasion as A or within 7 days of the administration of A.

Embodiment 9 provides a drug releasing implant, or arbitrary shape or in particulate form, composed of an hydratable ceramic, e.g. calcium sulphate and an active drug, e.g. an anti-androgen, or a combination of active drugs, the implant containing two or more distinguishable phases with different release rates for the active drug.

The implant is positioned in the prostate gland and provides a total release duration of 3 weeks to 6 months of the active drug(s). During the release period 30-50% of the drug is released during the first 1-7 days and 50-70% of the drug is released after 1 week to 6 months after positioning in the prostate gland.

Implants of this type of particular interest are prepared from:
250 mg of 2-hydroxyflutamide (e.g. Catalogue No. 161.01 from Micromol 2.25 g of calcium sulphate di-hydrate into which the 2-hydroxyflutamide is mixed, and 2.5 g of calcium sulphate hemi-hydrate (e.g. Product No 12090 from Riedel-de-Haen, or Product No. 30,766-1 from Sigma-Aldrich).
2.0 ml of water, suitably Product No 95280, Aqua Purificata, Ph Eur from Fluka.

From this pasty mix suitably 5 or 10 implants are moulded as e.g. rods or spheres and are made to cure before being positioned in the prostate gland through surgery.

In a separate aspect of the invention, it relates to the ue of a first and a second component for the preparation of a kit as defined herein for treatment of prostate related diseases.

It should be emphasized that all the details and particulars mentioned concerning any of the aspects of the invention apply also to the other aspects of the invention.

Active Substances for Use in a Method According to the Invention

In the present context, the term "active substance" is intended to denote a therapeutically, prophylactically and/or diagnostically active substance or a substance that has physiologic effect. The term is intended to include the active substance in any suitable form such as e.g. a pharmaceutically acceptable salt, complex, solvate or prodrug thereof of in any physical form such as, e.g., in the form of crystals, amorphous or a polymorphous form or, if relevant, in any stereoisomer form including any enantiomeric or racemic form, or a combination of any of the above.

In a method according to the invention, the one or more active substances is/are selected from the group comprising an androgen or a derivative thereof (including any salt form, any crystal form, any enantiomeric form), an anti-androgen or a derivative thereof, a nonsteroidal selective androgen receptor modulator or a derivative thereof, an oestrogen or a derivative thereof, an anti-oestrogen or a derivative thereof, a gestagen or a derivative thereof, an anti-gestagen or a derivative thereof, an oligonucleotide, a progestagen or a derivative thereof, a gonadotropin-releasing hormone or an analogue or derivative thereof, a gonadotropin inhibitor or a derivative thereof, a gonadotropin antagonists or a derivative thereof, an adrenal and/or prostate enzyme inhibitor, antibiotics, a cyclooxygenase inhibitor or a derivative thereof, an 5-alpha-reductase inhibitor, an alpha-adrenergic antagonist, a non-steroidal anti-inflammatory drug (NSAIDS), a corticosteroid, a HMG-CoA reductase inhibitor or a derivative thereof (statines), a membrane efflux and/or membrane transport protein, an immune system modulator, an angiogenesis inhibitor, and combinations thereof.

The therapeutically, prophylactically and/or diagnostically active drug substance(s) may also be in the form of a pharmaceutically acceptable salt, the active enantiomeric form, solvate or complex thereof or in any suitable crystalline or amorphous form or it may be in the form of a prodrug.

In a specific embodiment two active substances are used, one selected from anti-androgens and the other from gonadotropin-releasing hormones or analogues thereof.

In another specific embodiment the one or more active substances are selected from the group consisting of anti-androgens including flutamide, 2-hydroxy-flutamide, cyproteron acetate, megesterol acetate, nilutamide and bicalutamide, or the like. In a preferred aspect, the one or more active substances is 2-hydroxy-flutamide, flutamide or bicalutamide.

A combination of a non-steroidal antiandrogen, such as flutamide, 2-hydroxy-flutamide, bicalutamide, nilutamide or cyproterone acetate, megesterol acetate, together with 5-alpha reductase inhibitors, HMG-CoA reductase inhibitors (statines), cyclooxygenase inhibitors, non-steroidal anti-inflammatory drug (NSAIDS), corticosteroids, alpha-adrenergic antagonists, estrogens, anti-cancer medicines (such as cyclophosphamide, 5-fluorouracil, vincristine, cisplatin, epirubicin, taxotere), radiation enhancement factors (hypoxic cytotoxins), or growth and anti-growth factors may further improve the therapeutic effect for any prostate related disease such as those mentioned herein.

Moreover, any combination of active substances within one of the groups mentioned above or any combination of active substances from two or more of the groups mentioned above can be used in a method according to the invention or in a kit according to the invention. Without limiting the invention thereto, examples of suitable combinations for use according to the invention are given below.

Combinations of drug substance to be used in treatment of prostate cancer: hydroxyflutamide and finasteride in doses of 200-2000 mg and 0.5-4 mg, respectively, as an implant for at least two months treatment. A local boost dose, if any, can be between 0-25% of the dose such as, e.g., 5-25% of the dose. The boost dose may be for one or both drug substances and may be given by different compositions and/or other administration routes and the doses can be 250 mg and 1 mg for hydroxyflutamide and finasteride, respectively.

Combinations of drug substances to be used in treatment of benign prostate hyperthrophy (BPH): hydroxyflutamide and finasteride in doses of 200-2000 mg and 0.5-4 mg, respectively, as an implant for at least two months treatment. A local boost dose, if any, can be between 0-25% of the dose such as, e.g., 5-25% of the dose. The boost dose may be for one or both drug substances and may be given by different compositions and/or other administration routes and the doses should be 250 and 1 mg for hydroxyflutamide and finasteride, respectively.

Combinations of drug to be used in the LIDDS drug delivery technology for treatment of benign prostate hyperthrophy (BPH) and prostatite: hydroxyflutamide and finasteride in doses of 200-2000 mg and 0.5-4 mg as an implant for at least two months treatment. The boost dose locally can be between 0-25% of the dose such as, e.g., 5-25% of the dose. The boost dose may be for one or both drug substances and may be given by different compositions and/or other administration routes and the doses should be 250 and 1 mg for hydroxyflutamide and finasteride, respectively.

Drug to be used in treatment of prostatitis: ciprofloxacin.

Combinations of drug to be used in treatment of prostatitis: ciprofloxacin and an antibiotic.

Combinations of drug to be used in treatment of prostatitis: ciprofloxacin and naproxen (or any other NSAIDS).

Combinations of drug to be used in treatment of prostatitis: ciprofloxacin and prednisolone (or any other corticosteroid).

Pharmaceutical Compositions for Use in a Method of the Invention

A method according to the present invention may optionally involve two consecutive release rates of the active substance(s), one relatively fast release of the active substance(s) to obtain a boost or a burst dose and a second local controlled release rate of the same active substance(s) and/or prodrugs during a prolonged period of time in order to sustain the therapeutic effect.

The release that gives rise to the boost effect, if any, may be any suitable drug delivery system such as, e.g., oral, parenteral, nasal, rectal, pulmonary, transdermal, local, topical etc. administration and it may be in the form of e.g. solutions, suspensions, emulsions, syrups, sprays, tablets, capsules, sachets, powders, drops, crèmes, ointments, gels, hydrogels etc, or it may be provided by a freely releasable part of the active substance in biodegradable slow release formulations for local implantation.

Turning now to the controlled release drug delivery system, the carrier for the one or more active substances and/or prodrugs is a biodegradable hydrating ceramic or a mixture of biodegradable ceramic. The biodegradable hydrating ceramic is a non-hydrated, hydrated, semi-hydrated or partly hydrated ceramic selected from the group consisting of calcium sulphate, such as e.g., α-calcium sulphate, β-calcium sulphate, calcium sulphate hemihydrate; calcium phosphate, calcium carbonate, calcium fluoride, calcium silicate, magnesium sulphate, magnesium phosphate, magnesium carbonate, magnesium fluoride, magnesium silicate, barium sulphate, barium phosphate, barium carbonate, barium fluoride, barium silicate, hydroxyapatite or mixtures thereof. In a preferred aspect of the invention the biodegradable hydrating ceramic is non-hydrated, hydrated, semi-hydrated or partly hydrated calcium sulphate, such as e.g., α-calcium sulphate, β-calcium sulphate, calcium sulphate hemihydrate or mixtures thereof.

Use of a ceramic in a controlled release composition for use according to the invention is very suitable as it enable the preparation of a composition in dry form that immediately or substantially immediately before administration is mixed with an aqueous medium. In the thus obtained mixture the ceramic employed sorbs water and a curing process may begin, whereby the composition solidifies further. In other words, in a specific time period the composition has a sufficient fluidity (and viscosity) to enable administration via a syringe to the prostate tissue. This time period depends inter alia of the particular ceramic employed, addition of pharmaceutical excipients, if any, the one or more active substance employed, the constitution of aqueous medium employed as dispersion medium and of the individual amounts or concentrations used. Accordingly, by proper selection of the individual constituents and the amounts thereof it is possible to obtain a time window that is sufficient to enable administration of the composition. Once the composition is administered (e.g. by targeting the composition to the diseased tissue as described herein before), the composition rapidly solidifies, i.e. the active substance is immobilized in the diseased tissue as long as it is contained within the ceramic. The biodegradable ceramic controlled release formulation may also be used as pre-cured bodies that are implanted into the prostate gland or its vicinity. The preformed bodies may be in particulate form, which may be suspended in a liquid. The solidification process of this particular carrier material may thus take place both outside and/or inside the body.

The controlled release pharmaceutical composition is positioned in the prostate tissue, e.g. by ultrasound guidance or other relevant methods, and the implant (i.e. the solidified composition) provides an active substance concentration-time profile in the local tissue that is characterized by a prolonged release of the active substance. In the treatment of prostate cancer (PC), benign prostatic hyperplasia (BPH) or acute and chronic prostatitis the controlled active substance delivery rate may be adjusted for the expected decreased size/volume of the prostate tissue as a consequence of the anticipated pharmacological effect of the administered active substance.

Normally, the drug load of the active substance(s) in the controlled release pharmaceutical composition, i.e. the total amount of active substance(s) in comparison with the total weight of the controlled release composition, is in the range from about 0.1% w/w to about 50% w/w, such as from about 0.5% w/w to about 40% w/w, from about 1% w/w to about 30% w/w, from about 2% w/w to about 20% w/w, and preferably from about 5% w/w to about 10% w/w.

The active substance(s) is mixed into the ceramic prior to the solidification and is incorporated in a matrix of the ceramic material. Depending on the concentration of active substance and the details of the mixing procedure, the active substance may be present in different ways, such as on a molecular level, as a solid dispersion, as larger precipitates in different crystal and salt forms or in other ways.

In order to enable a rapid administration and to minimize inconvenience for the patient, if any, the present inventors have found, that the volume of the controlled release pharmaceutical composition administered to the prostate tissue should be in a range from about 0.05 ml to about 8 ml, such as from about 0.1 ml to about 6 ml, from about 0.25 ml to about 4 ml, and preferably from about 0.5 ml to about 2 ml. The volume may be divided into more than one injection (at substantially the same time) in order to spread the dosage over the whole or substantially the whole diseased prostate volume. The number of injections may be as many as 50, preferably less than 20.

With the method of the invention i) local application in soft tissue of a controlled release pharmaceutical composition containing active substance(s) and ii) targeted controlled release at or in the vicinity of the diseased tissue over a suitable period of time are made possible.

Such targeted and controlled delivery of the active substance(s), alone or in combination, optimizes the local concentration-time profile of the active substance(s) and their local pharmacological effect(s), and minimizes the systemic exposure, which is contemplated to reduce the side effects.

Release of Active Substance

The release rate from a controlled release implant is measurable in terms of reduced side effects, such as less diarrhea, or as reduced concentrations of the active metabolite in serum or tissues, or as reduced PSA values.

Controlled release here refers to a release prolonged in time over a period, which preferably exceeds the disposition half-time of the active drug substance in the relevant tissues. The concept/term of controlled release is essentially synonymous to prolonged, sustained, programmed, modified, or delayed release. Controlled release refers to a pre-determined release pattern, including or not including an initial burst. In the present context the term release is used essentially synonymous with the term delivery.

As mentioned above, the release of the active substance(s) from the controlled release composition take(s) place during a suitable period of time such as, e.g. from about 1 week to about 6 months in the treatment of prostate cancer (PC), benign prostatic hyperplasia (BPH) or acute and chronic prostatitis.

In a specific embodiment, at the most about 20% w/w of the one or more active substances (in total) contained in the controlled release pharmaceutical composition is released within at the longest 5 days after injection to a human, and/or at the most about 50% w/w of the active substance contained in the controlled release pharmaceutical composition is released 1 month or more after injection to a human.

Furthermore, or in an alternative embodiment, at the most about 75% w/w of the active substance contained in the controlled release pharmaceutical composition is released 1.5 month or more such as, e.g., 2 month or more after injection to a human, and/or at the most about 100% w/w of the active substance contained in the controlled release pharmaceutical composition is released 2 month or more such as 3 month or more or 6 months after injection to a human.

The following non-limiting examples are intended to illustrate the invention.

EXAMPLE 1

This in vivo example illustrates that it is feasible to administer locally into a dog prostate a ceramic-based controlled release pharmaceutical composition with 2-hydroxy-flutamide during anesthesia with current available insertion technologies and ultrasound guidance, and that the method provides a controlled release profile of the active substance at the site of application and action.

Methods and Materials

First, four male dogs (H1-H4) (Labrador, approx. 1 year of age and weight 30 kg) were given 2-hydroxy-flutamide (25 mg) by single bolus doses intravenously during 30 seconds. The intravenous solution base was sterile saline 54%, sterile polyethylene glycol 400 46% and ethanol (95%) 6%. Blood samples of 1.0 ml were taken from the Cephalic vein at 5, 10, 15, 30, 60, 90, 120, 240, 360, and 600 minutes. The blood samples were immediately centrifuged at 3000 rpm and the plasma samples were frozen at −80° C. until analysis.

One week later, the same animals were given 2-hydroxy-flutamide locally by a controlled release pharmaceutical composition in the prostate tissue. The 2-hydroxy- flutamide doses were 0 mg (H1), 30 mg (H3), 60 mg (H2) and 120 mg (H4), and each dog was given one implant only. Where H1 was a control given the composition without 2-hydroxy-flutamide. All doses of 2-hydroxy-flutamide were given after an overnight fast. Dog 1 (H1) and dog 3 (H3) were given an enema preoperatively. After the local prostate application of the pharmaceutical composition through rectum, an antibiotic (Quinolon) was administered in normal doses.

The controlled release pharmaceutical composition was composed of a calcium sulphate ceramic and 2-hydroxy-flutamide (Catalogue No. 161.01, from Micromol). To prepare the implant, a calcium sulfate hemi-hydrate (Calcium Sulfate-0.5-hydrate, Product No. 12090, from Riedel-de Haen) is mixed as a fine-grained powder with water and the active agent to form an injectable paste. The paste solidifies in-vivo in about 5 minutes to a solid implant. The ceramic powder to water ratio is 1:2 and the dose of active agent (30, 60 or 120 mg) is mixed with a total 0.8 ml of paste.

The controlled release pharmaceutical composition was inserted locally into the prostate tissue through needles by ultrasound guidance. The animals were under general anesthesia during the insertion procedure. The needle (15 cm long with an outer diameter of 0.9 mm) was inserted into the prepared rectum (an enema was given preoperatively) and was inserted through the rectal and abdominal wall and positioned in the prostate tissue by ultrasound guidance. The pharmaceutical composition was given as multiple thin strings of approximately 12 mm length and with a diameter of 1-2 mm.

After administration of the controlled release pharmaceutical composition in the prostate tissue, blood samples were taken during 3 weeks. Samples of 1.0 ml were taken from the Cephalic vein at day 0, after 6 hours and then in the morning at day 1, 2, 3, 4, 5, 6, 9, 12, 14, 16, 19 and 20 following the administration of the implant. The blood samples were immediately centrifuged at 3000 rpm and the plasma samples were frozen at −20° C. until analysis.

After day 20, each dog was terminated with an intravenous dose of a mixture of pentobarbital and potassium. The following organs were surgical removed and frozen: prostate, testis, liver and kidney for the assessment of effect and safety. These organs were carefully examined as a consequence of the local tissue exposure of 2-hydroxy-flutamide and the ceramic-based implant.

Quantification of 2-hydroxy-flutamide in plasma and tissue samples was done by HPLC-MS. HPLC was performed with a Surveyor HPLC system equipped with a CTC Pal autosampler. The analytical column was a Zorbax Eclipse XDB-18 (2.1 mm×50 mm, particle size 5 µm) connected to a guard column. The analytical column was a Zorbax Eclipse XDB-18 (2.1 mm×50 mm, particle size 5 µm) connected to a guard column. The eluent consisted of solvent A (aqueous formic acid 0.1%) and B (acetonitrile), a linear gradient from 25 to 90% of solvent B in 5 minutes was applied. The proportion of solvent B was then lowered to 25% in one minute and was allowed to equilibrate at this level for two minutes prior to the next injection. The volumetric flow-rate was 200 µL/min and the injection volume was 20 µL. The HPLC column outlet was coupled to a TSQ Quantum Ultra tandem triple quadrupole mass spectrometer (ThermoFinnigan, San José, Calif., USA). The transition of m/z 291 [M-H]$^-$→205 was used for 2-hydroxy-flutamide and m/z 316 [M-H]$^-$→273 was used for nilutamide (internal standard). The limit of quantification was 0.50 ng/ml in dog plasma. Calibration samples were prepared by spiking blank plasma samples with 100 µL of solutions of 2-hydroxy-flutamide at different concentrations. The calibration curves were constructed by linear regression of the peak area ratio of 2-hydroxy-flutamide and internal standard as a function of 2-hydroxy-flutamide concentrations. The method performance was studied using quality control (QC) samples, which were prepared by spiking blank plasma with 2-hydroxy-flutamide. The levels were 12, 120 and 610 ng/mL (n=3) for the lower calibration curve (0.5-1370 ng 2-hydroxy-flutamide/mL plasma) and at 0.12, 0.61 and 5.75 µg/mL (n=3) for the higher calibration curve (2.73-10.9 µg 2-hydroxy-flutamide/mL plasma). The accuracies of the analytical runs were calculated as 100*(mean determined concentration in QC sample/spiked concentration) % and the intra-run precisions were calculated as the relative standard deviation (RSD %) of the determined concentrations at each QC level.

Dog plasma (unknown, QC or calibration sample) at a volume of 100 µL was mixed with 100 µL of internal standard solution (nilutamide at 0.025 µg/mL) and 250 µL of acetonitrile. A subsequent vortex mix was performed for 20 seconds followed by a centrifugation for 10 minutes. 450 µL of the supernatant was transferred to a clean test tube and evaporated to dryness at 50° C. in a gentle stream of nitrogen. The residue was reconstituted in 100 µL aqueous formic acid (0.1%) and transferred to a vial for LC-MS/MS analysis. The data are presented in FIG. 1 and FIG. 2, for intravenous and local administration respectively.

The macroscopic pharmacological anti-proliferate effect of 2-hydroxy-flutamide was examined as the volume-weight ratio of the dog prostate tissue before and after the local administration of 2-hydroxy-flutamide as a single controlled release pharmaceutical composition.

Results

The animals had a normal behavior and accepted the controlled release pharmaceutical composition very well. After intravenous administration (when higher plasma exposure of 2-hydroxy-flutamide was experienced in all dogs) all dogs suffered from diarrhea, which was not observed in any animals after the local administration of the controlled release pharmaceutical composition in the dog prostate tissue.

The study clearly showed that it was feasible to administer a ceramic-based pharmaceutical composition containing 2-hydroxy-flutamide into the dog prostate tissue during anesthesia with current available insertion technologies during ultrasound guidance.

Figure 2:
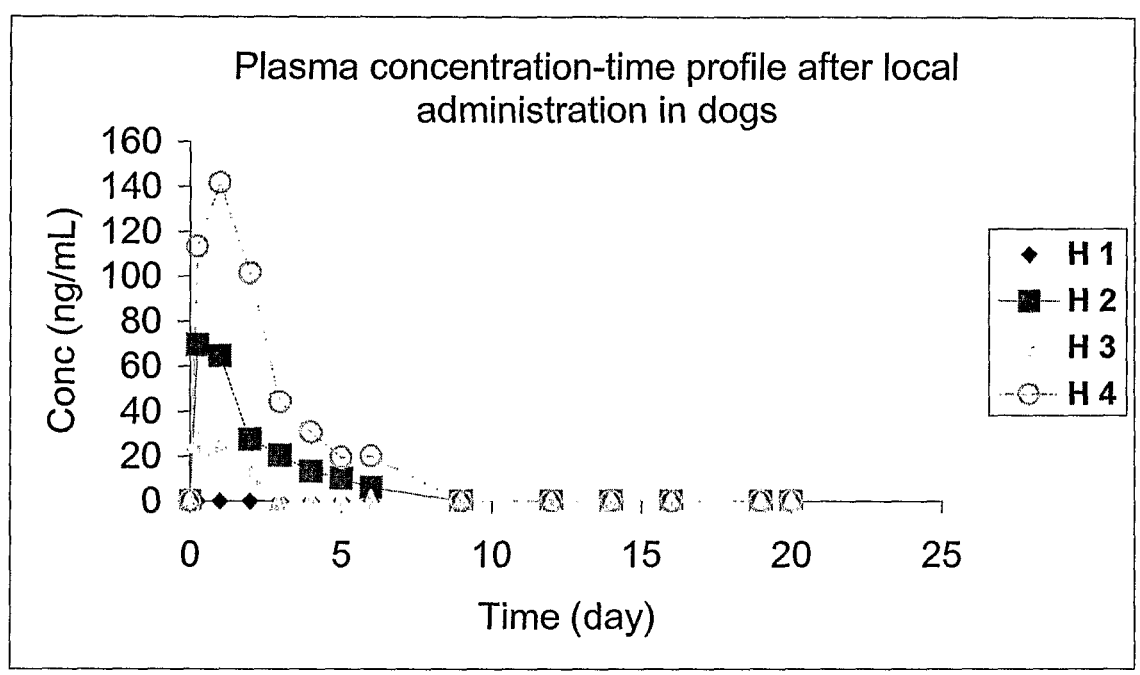
FIG. 2 is a plasma concentration-time profile after local administration in dogs in accordance with an embodiment of the present invention.

All pharmacokinetic variables for the intravenous injections are reported in Table 1 and the plasma concentration-time profile of 2-hydroxy-flutamide in each dog is given in FIG. 1. 2-Hydroxy-flutamide was rapidly eliminated after intravenous administration and the elimination half-life was 1.75±0.2.

TABLE 1

Pharmacokinetic variables of 2-hydroxy-flutamide after i.v. administration

| Animal No. | Dose (mg) | AUC (ng/ml * hrs) | Cl (ml/min) | V (l) | $t_{1/2}$ (hrs) | Cmax (ng/ml) |
|---|---|---|---|---|---|---|
| Dog 1 (H1) | 25 | 1260 | 330 | 49 | 1.70 | 639 |
| Dog 2 (H2) | 25 | 716 | 581 | 60 | 1.2 | 816 |
| Dog 3 (H3) | 25 | 1257 | 331 | 63 | 2.2 | 653 |
| Dog 4 (H4) | 25 | 1499 | 278 | 46 | 1.9 | 835 |

AUC = area under the plasma concentration-time curve,
Cl = clearance,
V = volume of distribution and
$t_{1/2}$ = elimination half-life.

It is showed that the release rate of 2-hydroxy-flutamide was significantly delayed with a ceramic-based controlled release pharmaceutical composition. When the drug substance was given in the composition the elimination half-life ranged from 35 to 45 hours for the three animals that were dosed (Table 2 and FIG. 2). Furthermore, the plasma concentration-time profiles of 2-hydroxy-flutamide after each composition dose were superimposable, i.e. the increase in plasma exposure (AUC) increased linearly with increased implant dose. This means that there was no irreversible binding and/or any non-linear processes involved in the delivery of the drug from the localised implant into the surrounding tissue. An approximation of the bioavailability of 2-hydroxy-flutamide from the intraprostate tissue was above 100% on average and it indicates that no major degradation of the active compound occurred within the prostate tissue.

TABLE 2

Pharmacokinetic variables of 2-hydroxy-flutamide after local administration

| Animal No. | Dose (mg) | AUC (ng/ml * hrs) | $C_{max}$ (ng/ml) | $t_{max}$ (hrs) | $t_{1/2}$ (hrs) |
|---|---|---|---|---|---|
| Dog 1 (H1) | | | | | |
| Dog 2 (H2) | 60 | 4024 | 69.5 | 6 | 45 |
| Dog 3 (H3) | 30 | 990 | 26.4 | 6 | 35 |
| Dog 4 (H4) | 120 | 9409 | 142 | 24 | 41 |

AUC = area under the plasma concentration-time curve,
$C_{max}$ = maximal plasma concentration,
$t_{max}$ = time to $C_{max}$,
$t_{1/2}$ = elimination half-life.

It is also shown that there is a large difference in systemic exposure of 2-hydroxy-flutamide between intravenous and local implant dosing as seen in Table 2. The maximal concentration ($C_{max}$) of 2-hydroxy-flutamide observed after intravenous dosing (25 mg) is about 6 times higher than the corresponding $C_{max}$-value observed after the local implant dosing (120 mg), see FIGS. 1 and 2. It is interesting to note that the maximum plasma concentration is 6 times higher despite that the intravenous dose is only one fifth (20%) of the local implant dose. The significantly higher plasma concentration (especially the peak concentration) achieved after intravenous dosing is also in accordance with the monitored diarrhea, a well-known side effect after oral therapy with flutamide.

There was a macroscopic effect observed based on the measured volume (before) and weight (after) following the local administration of 2-hydroxy-flutamide (Table 3). The obtained data suggests that the two higher doses (60 mg, H2 and 120 mg, H4) resulted in a macroscopic effect in comparison with the placebo (H1) and the low dose (30 mg, H3).

TABLE 3

Measured volume (before) and weight (after) of prostate tissue

| Animal No. | volume ($cm^3$) | Weight (g) | Dose (mg) | Palpation |
|---|---|---|---|---|
| Dog 1 (H1) | 11.9 | 17 | control | 0 |
| Dog 2 (H2) | 13.3 | 13 | 60 | ++ |
| Dog 3 (H3) | 12.4 | 17 | 30 | 0 |
| Dog 4 (H4) | 11.3 | 13 | 120 | +++ |

(0 = no effect, + = mild effect; ++ = intermediate; +++ = strong effect)

After three weeks of treatment the concentration of 2-hydroxy-flutamide was not possible to quantify in the prostate tissue. This is probably a consequence of a relatively rapid release of the drug days 0-7 direct after the insertion of the ceramic-based implant. Despite it was not possible to quantify the active drug substance in the prostate tissue it was possible to measure a clear anti-proliferate effect of 2-hydroxy-flutamide. This observation might be due to long effect duration of the active drug substance, which is supported by the slow proliferation of the prostate cells. Accordingly, intermittent endocrine treatment of prostate cancer is a treatment approach that is undergoing careful clinical investigation.

EXAMPLE 2

The major purpose of the present animal study was to examine the pharmacokinetics, efficacy and safety of the novel local drug delivery system with 2-hydroxyflutamide, a selective antagonist to the androgen receptor (AR). A ceramic based drug delivery product was administered into an androgen dependent tissue (the bulbourethral gland) in male sheep. In total 11 male sheep were divided into two separate groups. One group was given 2-hydroxyflutamide by the local implant delivery system as a single administration into the bulbourethral gland and was monitored during 2 months. Each sheep in this treatment group received the prostate implant by a single dose of 250 mg. The other group only received ceramic formulation without any active drug substance.

The implant drug delivery system was inserted locally, via rectum, into the androgen dependent tissue (bulbourethral gland) through sterile needles during rectal ultrasound guidance. The animals were during anaesthesia throughout the insertion procedure. The sterile ceramic based implant had two major components: calcium sulphate ($CaSO_4$-$0.5H_2O$) and 2-hydroxyflutamide. The composition of the formulation was 250 mg 2-hydroxyflutamide+2.25 g calcium sulphate di-hydrate+5.0 g calcium sulphate hemi-hydrate and it was mixed with solution: 3.5 ml of water solution (with 1% acetic acid and 1% methyl cellulose). The hence prepared compositions were packed in glass vials and sterilised with gamma radiation prior to us. The amount injected into each lobe of the androgen sensitive bulbourethral gland was about 2.0-3.0 ml.

Quantification of 2-hydroxy-flutamide in plasma samples was done by HPLC-MS. HPLC was performed with a Surveyor HPLC system equipped with a CTC Pal autosampler. The analytical column was a Zorbax Eclipse XDB-18 (2.1 mm×50 mm, particle size 5 μm) connected to a guard column. The calibration curves were constructed by linear regression of the peak area ratio of 2-hydroxy-flutamide and internal standard as a function of 2-hydroxy-flutamide concentrations. The method performance was studied using quality control (QC) samples, which were prepared by spiking blank plasma with 2-hydroxy-flutamide.

Sheep plasma (unknown, QC or calibration sample) at a volume of 100 μL was mixed with 100 μL of internal standard solution (nilutamide at 0.025 μg/mL) and 250 μL of acetonitrile. A subsequent vortex mix was performed for 20 seconds followed by a centrifugation for 10 minutes. 450 μL of the supernatant was transferred to a clean test tube and evaporated to dryness at 50° C. in a gentle stream of nitrogen. The residue was reconstituted in 100 μL aqueous formic acid (0.1%) and transferred to a vial for LC-MS/MS analysis.

The formulation was successfully administered in 11 male sheep. Based on the plasma exposure profile the pharmacokinetic variables were calculated with standard methods (Table 4).

TABLE 4

Pharmacokinetic variables of 2-hydroxy-flutamide following administration of a controlled release implant drug delivery system of 250 mg 2-hydroxy flutamide into the androgen dependent tissue (bulbourethral gland) in seven male sheep.

| Animal No. | Dose (mg) | AUC (ng/ml * hrs) | Cmax (ng/ml) | tmax (hrs) | t½ (hrs) |
|---|---|---|---|---|---|
| Sheep 3 | 250 | 4287 | 26 | 24 | 159 |
| Sheep 4 | 250 | 3725 | 84 | 6 | 253 |
| Sheep 6 | 250 | 3390 | 35 | 6 | 117 |
| Sheep 7 | 250 | 3755 | 19.8 | 6 | 67 |
| Sheep 8 | 250 | 1855 | 16.3 | 6 | 168 |
| Sheep 9 | 250 | 4948 | 34 | 6 | 119 |
| Sheep 12 | 250 | 4436 | 31 | 6 | 140 |
| Mean | | 3771 | 42 | 9 | 146 |
| SEM | | 993 | 24 | 7 | 58 |

Figure 3:
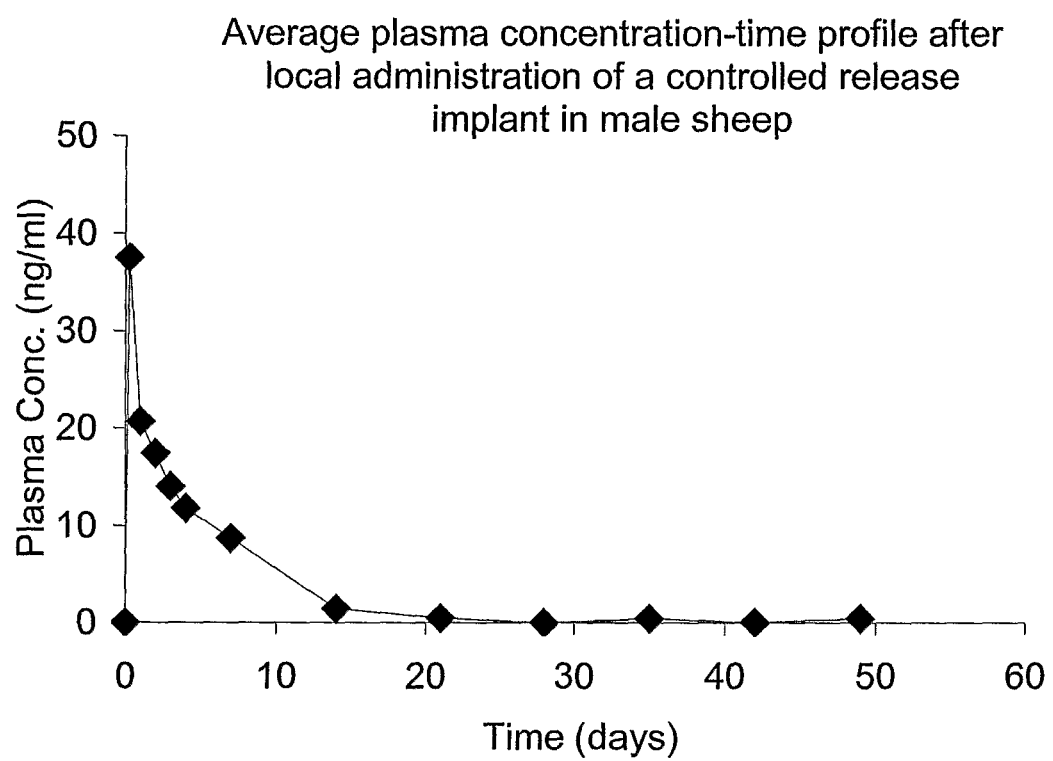
FIG. 3 is an average plasma concentration-time profile after local administration of a controlled release impant in male sheep in accordance with an embodiment of the present invention.
Figure 4:
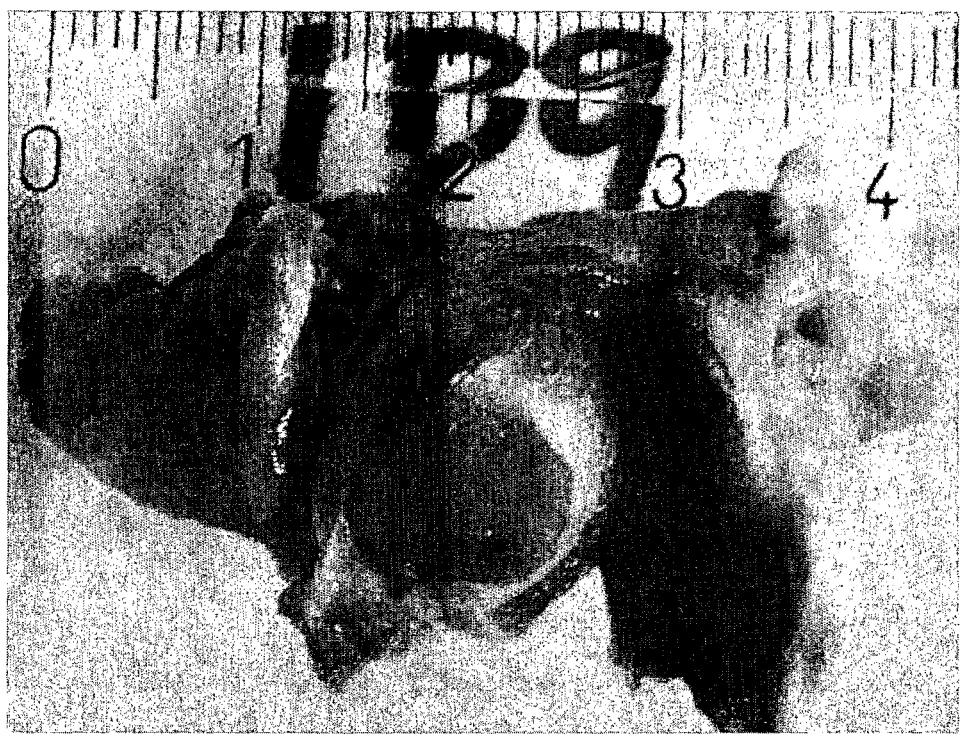
FIG. 4 is a photograph of the left lobe of a sheep bulbourethral gland after single intra-gland injection of a ceramic implant formulation in accordance with an embodiment of the present invention.

The elimination half-life was prolonged to about 146 hours, which is a consequence of a reduced drug release rate of 2-hydroxyflutamide from the controlled release formulation injected into the prostate gland. The first plasma concentration measured at 6 hours was also the highest, which confirms a relatively rapid drug release of the active drug just after insertion. This peak plasma concentration is considered to be favorable for the local pharmacological effect of 2-hydroxyflutamide. The plasma concentration was low through the experiment and there was no androgen dependent side effect observed. The average plasma concentration-time profile of 2-hydroxyflutamide is shown in FIG. 3. It was also possible to quantify levels of 2-hydroxyflutamide in prostate gland three moths after the injection. All together the prolonged half-life and the quantifiable intratissue amounts indicate that the release from the controlled release implant was successfully prolonged. At the same a macroscopic effect as indicated by the decreased volume and weight of the androgen dependent tissue (bulbourethral gland). The macroscopic effect of 2-hydroxy-flutamide on the volume of the bulbourethral gland after single intra-gland injection of the ceramic implant formulation into the left lobe (the section from 0 to 1 cm on the scale) of a sheep bulbourethral gland is shown in FIG. 4. The right lobe (the section from 1 to 4 cm on the scale) was untreated and had an intact volume. The untreated, right lobe has been cut through for evaluation purposes. The urethra is located at about 1.3 cm on the scale and runs vertically through the gland. The left and right lobes have the same size and volume when untreated.

These observations confirms the objective of the present investigation, which was to demonstrate that a controlled release implant of 2-hydroxyflutamide administered into the bulbourethral gland would result in low plasma concentrations and at the same time provide a local anti-androgen effect.

EXAMPLE 3

The overall aim of the current preclinical study was to further develop a novel local implant drug delivery system for specific and targeted anti-androgen therapy in the human prostate tissue. This strategy aims to develop innovative pharmaceutical products useful in the cancer treatment, which significantly contribute to more effective therapies with fewer side effects in various disease states where antagonistic action on the androgen receptor is a central function (such as prostate cancer, benign prostatic hyperplasia).

The major purpose of the present animal study was to examine the efficacy and safety of the new local drug delivery system with 2-hydroxyflutamide, a selective antagonist of the androgen receptor (AR) as the active moiety in human prostate tissue during various treatment periods in male dogs.

The dog has been selected as the test model because of its proven suitability in this type of study. The study was performed in 12 male beagle dogs from Harlan Winkelmann GmbH, Germany.

The sterile controlled release implant was composed of ceramic compounds and 2-hydroxyflutamide. Storage and handling instructions were given. The composition of the formulation of the low and high dose was 250 mg of 2-hydroxyflutamide +2.25 g calcium sulphate di-hydrat +5.0 g calcium sulphate hemi-hydrate and it was mixed with solution: 3.5 ml of water solution (with 1% acetic acid and 1% methyl cellulose).

The final formulation work was done during sterile conditions by trained personal at the experimental day. The amount injected into each lobe of the androgen sensitive bulbourethral gland was about 2.0-3.0 ml for the low dose (250 mg) and 4.0-6.0 ml of the high dose (500 mg).

The animals were fasted for at least 12 hours prior to the insertion procedure on Day 1. The implant drug delivery system was inserted locally into the prostate tissue, via rectum, through sterile needles during rectal ultrasound guidance. Each animal was under anesthesia during the insertion procedure.

The groups, dose levels, study duration and animal numbers are given in Table 5 below.

TABLE 5

| Group | Dose* (mg/implant) | Duration of study | Animal No |
|---|---|---|---|
| A | 250 | 3 months | 7-10 |
| B | 500 | 3 months | 11-14 |
| C | 500 | 6 months | 15-18 |

Blood samples for pharmacokinetic was collected as follows: On Day 1: Pre-insertion and 6 hours after insertion. Blood samples were sampled in the morning on Days 2, 3, 4, 5, 6 and 7. During the rest of the study blood samples were collected once a week.

Blood samples of approximately 3 ml were drawn from the jugular vein. The blood was sampled into vacutainers containing EDTA as anticoagulant. The blood was placed in ice water until centrifugation (10 min, 1270 G, +4° C.). The plasma was transferred to Nunc cryotubes (Nunc, Denmark) and frozen at −18° C. or below and sent with dry ice to Swedish Veterinary Institute, Uppsala for analysis.

The plasma pharmacokinetic variables were calculated using standard pharmacokinetic methods and are given for both implant doses of 250 mg and 500 mg in Tables 6 and 7. The bioavailability (F) was approximated by using the average value for clearance of 2-hydroyflutamide when it was given by an intravenous dose in the dog study presented in Example 1.

TABLE 6

Pharmacokinetic variables of hydroxy-flutamide after local implant dose of 250 mg in four animals.

| Animal No. | Dose (mg) | AUC (ng/ml * hrs) | Cmax (ng/ml) | tmax (hrs) | F (%) | t½ (hrs) |
|---|---|---|---|---|---|---|
| Dog 7 | 250 | 5446 | 58 | 6 | 46 | 34 |
| Dog 8 | 250 | 5921 | 85 | 6 | 50 | 39 |
| Dog 9 | 250 | 13237 | 131 | 6 | 112 | 26 |
| Dog 10 | 250 | 8701 | 97 | 48 | 74 | 32 |
| Mean | | 8326 | 93 | 17 | 71 | 33 |
| SEM | | 3575 | 30 | 21 | 30 | 5 |

TABLE 7

Pharmacokinetic variables of hydroxy-flutamide after local implant dose of 500 mg in four animals.

| Animal No. | Dose (mg) | AUC (ng/ml * hrs) | Cmax (ng/ml) | tmax (hrs) | F (%) | t½ (hrs) |
|---|---|---|---|---|---|---|
| Dog 11 | 500 | 13009 | 142 | 6 | 110 | 59 |
| Dog 12 | 500 | 13420 | 202 | 6 | 113 | 34 |
| Dog 13 | 500 | 11631 | 133 | 48 | 98 | 28 |
| Dog 14 | 500 | 10207 | 102 | 48 | 86 | 57 |
| Mean | | 12067 | 145 | 27 | 102 | 45 |
| SEM | | 1457 | 42 | 24 | 12 | 16 |

The plasma pharmacokinetic data (the elimination half-life) in the present animal study demonstrated than this version of the implant controlled release formulation had a more rapid release rate than the version used in the study in sheep presented in Example 2. This demonstrates that it is possible to adjust the drug release rate in vivo by using different compositions of such controlled release implant dosage forms. This will be very useful when treating different diseases in the prostate gland.

Figure 5:
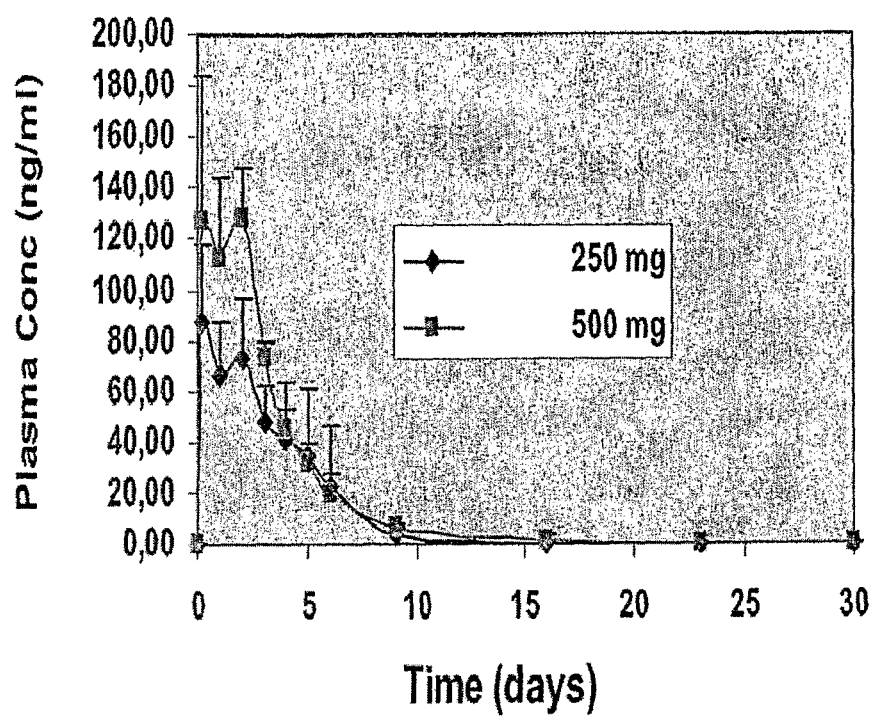
FIG. 5 is an average plasma concentration-time profile after prostate implantation in dogs in accordance with an embodiment of the present invention.

It was also clear that the animals were accepting the treatment well and no side-effects were observed. For instance, there was no diarrhea observed which was in accordance with the low plasma exposure of the anti-androgen 2-hydroxyflutamide. The average plasma concentration-time profiles for the 250 mg and 500 mg dose are given in FIG. 5. The high bioavailability of 2-hydroxyflutamide observed following intraprostate injection of the controlled release formulation indicates that not significant degradation occurred in the prostate gland. There was no effect of the treatment on the urinated volume in the dogs, which clearly shows that the dosing procedure of the present controlled release implant is well accepted in vivo. Microscopic findings of the prostate tissue by using histopathology analysis showed there was a increased incidence of vacuolation and cystic acini in the groups treated with 2-hydroxyflutamide, which is in accordance with the expected atrophy of the gland as a consequence of local exposure of an anti-androgen such as 2-hydroxyflutamide. All together, these local effects and absence of side-effect confirm the clinical rational performance of the present local controlled release implant.

EXAMPLE 4

Planned Preclinical Study

An Open, Parallel Group Design Study of Finasteride in Rats or Dogs

Study No. 1

The purpose is to investigate the pharmacokinetic and pharmacodynamics of finasteride in doses of 0.2-4 mg as a controlled release implant for at least three weeks to six months treatment. Finasteride is a 5-α-reducatse inhibitor and will reduce the local formation of dihydrotestosterone in the prostate gland.

The hypothesis is that the safety and efficacy of the treatment of prostate cancer can be obtained by a using finasteride for the local treatment of prostate cancer and/or benign prostate hyperthrophy (BPH).

The objective of the study is to assess the safety and efficacy of different doses of finasteride for an improved local controlled release treatment of prostate cancer and/or benign prostate hyperthrophy (BPH).

The study design will be as follows: An open, parallel group design, dose-finding study (pre-clinical phase) of finasteride will be done in 28 male animals (rat or dogs).

Finasteride will be given in doses of 0.5-5 mg as a controlled release implant for at least three weeks to six months treatment. 0.5-5 mg of finasteride 2.25 g+calcium sulphate di-hydrat+5.0 g calcium sulphate hemi-hydrat will be mixed with solution: 3.5 ml of water solution (with 1% acetic acid and 1% methyl cellulose).

Blood samples for the determination of finasteride will be taken at pre-dose and 6 hours and then once a week after the administration of the study drugs. The blood samples are taken from a peripheral vein. Each blood sample is centrifuged and plasma is sampled in a separate tube and all samples are kept frozen (−70 C) until analysis.

On each study day the animals will be given the drug in the fasted state. The drug administration is given according to standard procedure at the laboratory where the study is conducted. The implant drug delivery system will be inserted locally into the prostate tissue, via rectum, through sterile needles during rectal ultrasound guidance. The animals will be under anesthesia during the insertion procedure.

The effect of the treatment will be monitored both regarding side-effects and local effect evaluation. The pharmacodynamic variables, such as local histopathology and macroscopic effects (weight/volume) will be analysed by standard pharmacodynamic assessment.

The pharmacokinetic variables for each drug will be calculated using non-compartmental analysis and WinNonlin 4.0 (Pharsight Corp., Mountain View, Calif., USA). The maximal peak plasma concentrations ($C_{max}$) and the times at which the maximum peaks occurred ($t_{max}$) will be derived directly from the plasma-concentration-time profile. The apparent terminal elimination half-life ($t_{1/2}$) will be obtained from $k_e$.

The inclusion criteria are: Male rats, weighing about 250 g and male dogs, weighing about 10-20 kg.

The effect variables are: Pharmacodynamic variables of the study drug. Pharmacokinetic variables and plasma concentration profiles of the study drug.

EXAMPLE 5

Planned Preclinical Study

An Open, Parallel Group Design Study of 2-Hydroxyflutamide and Finasteride in Rats or Dogs Study No. 2

The purpose is to investigate the pharmacokinetic and pharmacodynamics of a combination of 2-hydroxyflutamide and finasteride in doses of 200-4000 mg and 0.5-4 mg as a controlled release implant for at least three weeks to six months treatment. 2-hydroflutamide is a pure anti-androgen compound finasteride is a 5-α-reducatse inhibitor. The 2-hydroxuflutamide will act as an antagonist at androgen receptor (AR) in the prostate gland and finasteride will reduce the local formation of dihydrotestosterone in the prostate gland.

The hypothesis is that the safety and efficacy of the local controlled release implant treatment of prostate cancer and/or benign prostate hyperthrophy (BPH) can be obtained by a using a combination 2-hydroxyflutamide and finasteride.

The objective of the study is to assess the safety and efficacy of different doses of a combination of 2-hydroxyflutamide and finasteride for an improved local controlled release treatment of prostate cancer and/or benign prostate hyperthrophy (BPH).

The study design is planned to be as follows:

An open, parallel group design, dose-finding study (preclinical phase) of a combination of 2-hydroxyflutamide and finasteride will be done in 28 male animals (rat or dogs).

2-hydroxyflutamide and finasteride will be given in doses of 200-4000 mg and 0.5-5 mg as a controlled release implant for at least three weeks to six months treatment. 200-4000 mg of 2-hydroxyflutamide+0.5-5 mg of finasteride+2.25 g calcium sulphate di-hydrat+5.0 g calcium sulphate hemi-hydrat will be mixed with solution: 3.5 ml of water solution (with 1% acetic acid and 1% methyl cellulose).

Blood samples for the determination of 2-hydroxyflutamide and finasteride will be taken at pre-dose and 6 hours and then once a week after the administration of the study drugs. The blood samples are taken from a peripheral vein. Each blood sample is centrifuged and plasma is sampled in a separate tube and all samples are kept frozen (−70 C) until analysis.

On each study day the animals will be given the drug in the fasted state. The drug administration is given according to standard procedure at the laboratory where the study is conducted. The implant drug delivery system will be inserted locally into the prostate tissue through sterile needles during rectal ultrasound guidance. The animals will be under anesthesia during the insertion procedure.

The effect of the treatment will be monitored both regarding side-effects and local effect evaluation. The pharmacodynamic variables, such as local histopathology and macroscopic effects (weight/volume) will be analysed by standard pharmacodynamic assessment.

The pharmacokinetic variables for each drug will be calculated using non-compartmental analysis and WinNonlin 4.0 (Pharsight Corp., Mountain View, Calif., USA). The maximal peak plasma concentrations ($C_{max}$) and the times at which the maximum peaks occurred ($t_{max}$) will be derived directly from the plasma-concentration-time profile. The apparent terminal elimination half-life ($t_{1/2}$) will be obtained from $k_e$.

Inclusion criteria: Male rats, weighing about 250 g and male dogs, weighing about 10-20 kg.

Effect variables: Pharmacodynamic variables of both drugs. Pharmacokinetic variables and plasma concentration profiles of both drugs.

Time schedule: about 1-2 years

EXAMPLE 6

Planned Preclinical Study

An Open, Parallel Group Design Study of Doxazosin and Finasteride in Rats or Dogs Study No. 3

Purpose of the study is to investigate the pharmacokinetic and pharmacodynamics of a combination of doxazosin and finasteride in doses of 4-40 mg and 0.5-4 mg as a controlled release implant for at least three weeks to six months treatment. Doxazosin is an α-adrenergic antagonist compound finasteride is a 5-α-reducatse inhibitor. Doxazosin will act as a selective antagonist at α-adrenergic receptor in the muscle of the prostate gland and finasteride will reduce the local formation of dihydrotestosterone in the prostate gland.

The hypothesis is that the safety and efficacy of the local controlled release implant treatment of benign prostate hyperthrophy (BPH) can be obtained by a using a combination doxazosin and finasteride.

The objective of the study is to assess the safety and efficacy of different doses of a combination of doxazosin and finasteride for an improved local controlled release treatment of benign prostate hyperthrophy (BPH).

The study design is planned to be as follows:

An open, parallel group design, dose-finding study (preclinical phase) of a combination of doxazosin and finasteride will be done in 28 male animals (rat or dogs).

Doxazosin and finasteride will be given in doses of 4-40 mg and 0.5-5 mg as a controlled release implant for at least three weeks to six months treatment. The composition will be made from a mixture of the following powders: 4-40 mg of doxazosin+0.5-5 mg of finasteride+2.25 g calcium sulphate di-hydrat+5.0 g calcium sulphate hemi-hydrat will be mixed with solution: 3.5 ml of water solution (with 1% acetic acid and 1% methyl cellulose).

Blood samples for the determination of doxazosin and finasteride will be taken at pre-dose and 6 hours and then once a week after the administration of the study drugs. The blood samples are taken from a peripheral vein. Each blood sample is centrifuged and plasma is sampled in a separate tube and all samples are kept frozen (−70 C) until analysis.

On each study day the animals will be given the drug in the fasted state. The drug administration is given according to standard procedure at the laboratory where the study is conducted. The implant drug delivery system will be inserted locally into the prostate tissue through sterile needles during rectal ultrasound guidance. The animals will be under anesthesia during the insertion procedure.

The effect of the treatment will be monitored both regarding side-effects and local effect evaluation. The pharmacodynamic variables, such as local histopathology and macroscopic effects (weight/volume) will be analysed by standard pharmacodynamic assessment.

The pharmacokinetic variables for each drug will be calculated using non-compartmental analysis and WinNonlin 4.0 (Pharsight Corp., Mountain View, Calif., USA). The maximal peak plasma concentrations ($C_{max}$) and the times at which the maximum peaks occurred ($t_{max}$) will be derived directly from the plasma-concentration-time profile. The apparent terminal elimination half-life ($t_{1/2}$) will be obtained from $k_e$.

The inclusion criteria are: Male rats, weighing about 250 g and male dogs, weighing about 10-20 kg.

The effect variables are: Pharmacodynamic variables of both drugs. Pharmacokinetic variables and plasma concentration profiles of both drugs.

Time schedule is planned to be 1-2 years from the start of the study.

EXAMPLE 7

An Open, Parallel Group Design Study of Ciprofloxacin in Rats or Dogs—Planned Study Study No. 4

The purpose is to investigate the pharmacokinetic and pharmacodynamics of ciprofloxacin in dose of 500-5000 mg as a controlled release implant for at least one week to six weeks treatment. Ciprofloxacin is used against bacterial prostatitis.

The hypothesis is that the safety and efficacy of the local controlled release implant treatment of acute and chronic bacterial prostatitis can be obtained by a using a ciprofloxacin. An intraprostate injection may increase the effect on bacteria due to better availability in the infected organ.

The objective of the study is to assess the safety and efficacy of different doses of ciprofloxacin for an improved local controlled release treatment of acute and chronic bacterial prostatitis.

The study design will be as follows: An open, parallel group design, dose-finding study (pre-clinical phase) of a ciprofloxacin will be done in 28 male animals (rat or dogs). Ciprofloxacin will be given in doses of 500 to 5000 mg as a controlled release implant for at least one week to six weeks treatment. The composition is made from a mixture of the following powders: 500-5000 mg of ciprofloxacin+2.25 g calcium sulphate di-hydrat+5.0 g calcium sulphate hemi-hydrat will be mixed with solution: 3.5 ml of water solution (with 1% acetic acid and 1% methyl cellulose).

Blood samples for the determination of ciprofloxacin will be taken at pre-dose and 6 hours and then once a week after the administration of the study drugs. The blood samples are taken from a peripheral vein. Each blood sample is centrifuged and plasma is sampled in a separate tube and all samples are kept frozen (−70 C) until analysis.

On each study day the animals will be given the drug in the fasted state. The drug administration is given according to standard procedure at the laboratory where the study is conducted. The implant drug delivery system will be inserted locally into the prostate tissue, via rectum, through sterile needles during rectal ultrasound guidance. The animals will be under anesthesia during the insertion procedure.

The effect of the treatment will be monitored both regarding side-effects and local effect evaluation. The pharmacodynamic variables, such as local histopathology, macroscopic effects (weight/volume) and remaining bacterial activity will be analysed by standard pharmacodynamic assessment.

The pharmacokinetic variables for each drug will be calculated using non-compartmental analysis and WinNonlin 4.0 (Pharsight Corp., Mountain View, Calif., USA). The maximal peak plasma concentrations ($C_{max}$) and the times at which the maximum peaks occurred ($t_{max}$) will be derived directly from the plasma-concentration-time profile. The apparent terminal elimination half-life ($t_{1/2}$) will be obtained from $k_e$.

The inclusion criteria are: Male rats, weighing about 250 g and male dogs, weighing about 10-20 kg.

The effect variables are: Pharmacodynamic variables of ciprofloxacin. Pharmacokinetic variables and plasma concentration profiles of ciprofloxacin.

EXAMPLE 8

An Open, Parallel Group Design Study of Ciprofloxacin and Naproxen in Rats or Dogs—Planned Study Study No. 5

The purpose is to investigate the pharmacokinetic and pharmacodynamics of ciprofloxacin and naproxen given in a combination of doses of 500-5000 mg and 200-5000 mg as a controlled release implant for at least one week to six weeks treatment. Ciprofloxacin is used against bacterial prostatitis and naproxen against inflammation.

The hypothesis is that the safety and efficacy of the local controlled release implant treatment of acute and chronic bacterial prostatitis can be obtained by a using a combination of ciprofloxacin and naproxen. An intraprostate injection may increase the effect on bacteria due to better availability in the infected organ. An improved anti-inflammatory effect is also possible to achieve by local dosing.

The objective is to assess the safety and efficacy of different doses of a combination of ciprofloxacin and naproxen for an improved local controlled release treatment of acute and chronic bacterial prostatitis.

The study design will be as follows: An open, parallel group design, dose-finding study (pre-clinical phase) of a combination of ciprofloxacin and naproxen will be done in 28 male animals (rat or dogs).

A combination of ciprofloxacin (500 to 5000 mg) and naproxen (200-5000 mg) will be given as a controlled release implant for at least one week to six weeks treatment. The composition is made from a mixture of the following powders: 500-5000 mg of ciprofloxacin+naproxen 200-5000 mg 2.25 g calcium sulphate di-hydrat+5.0 g calcium sulphate hemi-hydrat will be mixed with solution: 3.5 ml of water solution (with 1% acetic acid and 1% methyl cellulose).

Blood samples for the determination of ciprofloxacin and naproxen will be taken at pre-dose and 6 hours and then once a week after the administration of the study drugs. The blood samples are taken from a peripheral vein. Each blood sample is centrifuged and plasma is sampled in a separate tube and all samples are kept frozen (−70 C) until analysis.

On each study day the animals will be given the drug in the fasted state. The drug administration is given according to standard procedure at the laboratory where the study is conducted. The implant drug delivery system will be inserted locally into the prostate tissue, via rectum, through sterile needles during rectal ultrasound guidance. The animals will be under anesthesia during the insertion procedure.

The effect of the treatment will be monitored both regarding side-effects and local effect evaluation. The pharmacodynamic variables, such as local histopathology, macroscopic effects (weight/volume) and remaining bacterial activity will be analysed by standard pharmacodynamic assessment.

The pharmacokinetic variables for each drug will be calculated using non-compartmental analysis and WinNonlin 4.0 (Pharsight Corp., Mountain View, Calif., USA). The maximal peak plasma concentrations ($C_{max}$) and the times at which the maximum peaks occurred ($t_{max}$) will be derived directly from the plasma-concentration-time profile. The apparent terminal elimination half-life ($t_{1/2}$) will be obtained from $k_e$.

The inclusion criteria are: Male rats, weighing about 250 g and male dogs, weighing about 10-20 kg.

The effect variables are: Pharmacodynamic variables of both drugs. Pharmacokinetic variables and plasma concentration profiles of both drugs.

EXAMPLE 9

An Open, Parallel Group Design Study of Ciprofloxacin and Prednisolone in Rats or Dogs—Planned Study No. 6

The purpose is to investigate the pharmacokinetic and pharmacodynamics of ciprofloxacin and prednisolone given in a combination of doses of 500-5000 mg and 10-300 mg as a controlled release implant for at least one week to six weeks treatment. Ciprofloxacin is used against bacterial prostatitis and prednisolone against inflammation.

The hypothesis is that the safety and efficacy of the local controlled release implant treatment of acute and chronic bacterial prostatitis can be obtained by a using a combination of ciprofloxacin and prednisolone. An intraprostate injection may increase the effect on bacteria due to better availability in the infected organ. An improved anti-inflammatory effect is also possible to achieve by local dosing.

The objective of the study is to assess the safety and efficacy of different doses of a combination of ciprofloxacin and prednisolone for an improved local controlled release treatment of acute and chronic bacterial prostatitis.

The study design will be as follows: An open, parallel group design, dose-finding study (pre-clinical phase) of a combination of ciprofloxacin and naproxen will be done in 28 male animals (rat or dogs).

A combination of ciprofloxacin (500 to 5000 mg) and prednisolone (10-300 mg) will be given as a controlled release implant for at least one week to six weeks treatment. The composition is made from a mixture of the following powders: 500-5000 mg of ciprofloxacin+prednisolone 10-300 mg 2.25 g calcium sulphate di-hydrat+5.0 g calcium sulphate hemi-hydrate will be mixed with solution: 3.5 ml of water solution (with 1% acetic acid and 1% methyl cellulose).

Blood samples for the determination of ciprofloxacin and prednisolone will be taken at pre-dose and 6 hours and then once a week after the administration of the study drugs. The blood samples are taken from a peripheral vein. Each blood sample is centrifuged and plasma is sampled in a separate tube and all samples are kept frozen (−70 C) until analysis.

On each study day the animals will be given the drug in the fasted state. The drug administration is given according to standard procedure at the laboratory where the study is conducted. The implant drug delivery system will be inserted locally into the prostate tissue, via rectum, through sterile needles during rectal ultrasound guidance. The animals will be under anesthesia during the insertion procedure.

The effect of the treatment will be monitored both regarding side-effects and local effect evaluation. The pharmacodynamic variables, such as local histopathology, macroscopic effects (weight/volume) and remaining bacterial activity will be analysed by standard pharmacodynamic assessment.

The pharmacokinetic variables for each drug will be calculated using non-compartmental analysis and WinNonlin 4.0 (Pharsight Corp., Mountain View, Calif., USA). The maximal peak plasma concentrations ($C_{max}$) and the times at which the maximum peaks occurred ($t_{max}$) will be derived directly from the plasma-concentration-time profile. The apparent terminal elimination half-life ($t_{1/2}$) will be obtained from $k_e$.

The inclusion criteria are: Male rats, weighing about 250 g and male dogs, weighing about 10-20 kg.

The effect variables are: Pharmacodynamic variables of both drugs. Pharmacokinetic variables and plasma concentration profiles of both drugs.

EXAMPLE 10

An Open, Parallel Group Design Study of Cyclophosphamide and Taxotere in Rats or Dogs—Planned Study No. 7

The purpose is to investigate the pharmacokinetic and pharmacodynamics of cyclophosphamide and taxotere given in a combination of doses of 50-1500 mg/m2 and 5-150 mg/m2 as a controlled release implant for at least one day to fourteen days treatment. Cyclophosphamide and taxotere are used for cancer treatment.

The hypothesis is that the safety and efficacy of the local controlled release implant treatment used for cancer treatment can be obtained by a using a combination of cyclophosphamide and taxotere. An intraprostate injection may increase the effect on prostate cancer due to better availability in the tumour.

The objective is to assess the safety and efficacy of different doses of a combination of cyclophosphamide and taxotere for an improved local controlled release treatment of cancer.

The study design will be as follows: An open, parallel group design, dose-finding study (pre-clinical phase) of a combination of cyclophosphamide and taxotere will be done in 28 male animals (rat or dogs).

A combination of pharmacodynamics of cyclophosphamide (50-1500 mg/m2) and taxotere (5-150 mg/m2) will be given as a controlled release implant for at least one day to fourteen days treatment. The composition is made from a mixture of the following powders: 20-750 mg of cyclophosphamide+taxotere 2-80 mg 2.25 g calcium sulphate di-hydrat+5.0 g calcium sulphate hemi-hydrat will be mixed with solution: 3.5 ml of water solution (with 1% acetic acid and 1% methyl cellulose).

Blood samples for the determination of cyclophosphamide and taxotere will be taken at pre-dose and 6 hours and then once a week after the administration of the study drugs. The blood samples are taken from a peripheral vein. Each blood sample is centrifuged and plasma is sampled in a separate tube and all samples are kept frozen (−70 C) until analysis.

On each study day the animals will be given the drug in the fasted state. The drug administration is given according to standard procedure at the laboratory where the study is conducted. The implant drug delivery system will be inserted locally into the prostate tissue, via rectum, through sterile needles during rectal ultrasound guidance. The animals will be under anesthesia during the insertion procedure.

The effect of the treatment will be monitored both regarding side-effects and local effect evaluation. The pharmacodynamic variables, such as local histopathology and macroscopic effects (weight/volume) will be analysed by standard pharmacodynamic assessment.

The pharmacokinetic variables for each drug will be calculated using non-compartmental analysis and WinNonlin 4.0 (Pharsight Corp., Mountain View, Calif., USA). The maximal peak plasma concentrations ($C_{max}$) and the times at which the maximum peaks occurred ($t_{max}$) will be derived directly from the plasma-concentration-time profile, The apparent terminal elimination half-life ($t_{1/2}$) will be obtained from $k_e$.

The inclusion criteria are: Male rats, weighing about 250 g and male dogs, weighing about 10-20 kg.

The effect variables are: Pharmacodynamic variables of both drugs. Pharmacokinetic variables and plasma concentration profiles of both drugs.

The invention claimed:

1. A method for treating prostate related diseases in a subject, the method comprising
   i) administering to the subject an initial boost dose of one or more active substances, wherein said one or more active substances is flutamide, 2-hydroxy-flutamide, cyproterone acetate, nilutamide, or bicalutamide, or a pharmaceutically acceptable salt crystal or enantiomeric form thereof, or a combination thereof, and
   ii) administering locally into the prostate a controlled release pharmaceutical composition comprising one or more active substances, wherein said one or more, active substances is flutamide, 2-hydroxy-flutamide, cyproterone acetate, nilutamide, or bicalutamide, or a pharmaceutically acceptable salt, crystal or enantiomeric form thereof, or a combination thereof, in a biodegradable ceramic carrier.

2. The method according to claim 1, wherein the positioning of the controlled release pharmaceutical composition is monitored during injection by ultrasound imaging; magnetic resonance imaging; X-ray transmission imaging; computer tomography imaging; isotope based imaging including positron emission tomography or gamma camera/ SPECT; magnetic- or radio-wave based positioning systems.

3. The method according to claim 1, further comprising a step of in vivo monitoring the release rate of the one or more active substances by monitoring the degradation of the controlled release pharmaceutical composition by ultrasound imaging; magnetic resonance imaging; X-ray transmission imaging; computer tomography imaging; isotope based imaging including positron emission tomography or gamma camera/ SPECT; magnetic- or radio-wave based positioning systems.

4. The method according to claim 1, further comprising a step of in vivo monitoring the release rate of the one or more active substances by monitoring the plasma levels of the one or more active substances.

5. The method according to claim 3, wherein the monitoring of the degradation is done at predetermined intervals after the first injection of the controlled release pharmaceutical composition.

6. The method according to claim 5, further comprising administering one or more supplemental doses of the one or more active substances when the monitoring of the degradation shows a significant degradation of the controlled release pharmaceutical composition.

7. The method according to claim 6, wherein the dose is a boost dose of the one or more active substances.

8. The method according to claim 6, wherein the dose is administered in the form of a controlled release pharmaceutical composition of the same one or more active substances.

9. The method according to claim 1, farther comprising repeating step ii) of claim 1 at a predetermined time after injection of the first injected controlled release pharmaceutical composition.

10. The method according to claim 1, wherein the drug load of the one or more active substances in the controlled release pharmaceutical composition is in the range from about 0.1% w/w to about 50% w/w.

11. The method according to claim 1, wherein the volume of the controlled release pharmaceutical composition administered is in a range from about 0.05 ml to about 8 ml.

12. The method according to claim 1, wherein the active substance is 2-hydroxy-flutamide, flutamide or bicalutamide.

13. The method according to claim 1, wherein the active substance is 2-hydroxy-flutamide or flutamide.

14. The method according to claim 1, wherein the active substance in step i) and ii) is 2-hydroxy-flutamide.

15. The method according to claim 1, wherein the active substance in step i) is flutamide and the active substance in step ii) is 2-hydroxy-flutamide.

16. The method according to claim 1, wherein the active substance is bicalutamide.

17. The method according to claim 1, wherein the active substance in step i) and ii) is bicalutamide.

18. The method according to claim 13, wherein the boost dose in step i) is in a range of from about 100 mg to about 2000 mg per day for oral administration.

19. The method according to claim 13, wherein the boost dose in step i) is in a range of from about 1 mg to about 100 mg per day for local administration in the prostate.

20. The method according to claim 16, wherein the boost dose in step i) is in a range of from about 10 mg to about 1000 mg per day for oral administration.

21. The method according to claim 16, wherein the boost dose in step i) is in a range of from about 1 mg to about 50 mg per day for local administration in the prostate.

22. The method according to claim 12, wherein the controlled release pharmaceutical composition in step ii) provides an amount of the active substance in a range of from about 0.1 mg to about 100 mg per day in the prostate.

23. The method according to claim 1, wherein the administration i) and ii) are substantially simultaneous.

24. The method according to claim 1, wherein the administration i) and ii) are separate in time by less than 24 hours.

25. The method according to claim 13, wherein the local concentration of 2-hydroxy-flutamide in the prostate tissue is in a range of from about 0.001 nM to about 10.0 µM at steady state for a time period of from about 1 to about 6 months after administration of the first, or any supplemental, injection of the controlled release pharmaceutical composition.

26. The method according to claim 12, wherein the plasma concentration of 2-hydroxy-flutamide or bicalutamide is reduced to at least 25% or less of the values obtained after oral administration of a standard flutamide composition in a daily dose that provides an equivalent therapeutic effect.

27. The method according to claim 12, wherein the local concentration of 2-hydroxy-flutamide or bicalutamide in the liver tissue is at least 5 times less than that obtained dining the absorption phase after oral administration of a standard flutamide or bicalutamide composition in a daily dose that provides an equivalent therapeutic effect.

28. The method according to claim 12, wherein the treatment gives a reduction in dose dependent side effects selected from the group consisting of diarrhea, breast enlargement, nausea, impotence, decreased libido, abdominal pain, flatulence, tiredness, asthenia, osteoporosis, sweating, hot flushes, loss of libido or erectile function, weight gain, gynaecomastia, and liver toxicity compared to that obtained after oral administration of a standard flutamide or bicalutamide composition in a daily dose that provides an equivalent therapeutic effect.

29. The method according to claim 1, wherein the biodegradable ceramic is a biodegradable hydrating ceramic selected from the group consisting of non-hydrated or hydrated calcium sulphate, calcium phosphate, calcium carbonate, calcium fluoride, calcium silicate, magnesium sulphate, magnesium phosphate, magnesium carbonate, magnesium fluoride, magnesium silicate, barium sulphate, barium phosphate, barium carbonate, barium fluoride, and barium silicate, or mixtures thereof.

30. The method according to claim 29, wherein the biodegradable hydrating ceramic is non-hydrated or hydrated calcium sulphate.

31. The method according to claim 1, wherein at the most about 20% w/w of the one or more active substances contained in the controlled release pharmaceutical composition is released within 5 days or less after injection to a human.

32. The method according to claim 1, wherein at the most about 50% w/w of the active substance contained in the controlled release pharmaceutical composition is released 1 month or more after injection to a human.

33. The method according to claim 1, wherein at the most about 75% w/w of the active substance contained in the controlled release pharmaceutical composition is released 1.5 month or more after injection to a human.

34. The method according to claim 1, wherein at the most about 100% w/w of the active substance contained in the controlled release pharmaceutical composition is released 2 months or more after injection to a human.

35. A kit for use in treatment of prostate related diseases as recited in claim 1, comprising:

i) a first component giving an initial boost dose of one or more active substances, wherein said one or more active substances is flutamide, 2-hydroxy-flutamide, cyproterone acetate, nilutamide, or bicalutamide, or a pharmaceutically acceptable salt, crystal or enantiomeric form thereof, or a combination thereof; and ii) a second component comprising a controlled release pharmaceutical composition comprising one or more active substances, wherein said one or more active substances is flutamide, 2-hydroxy-flutamide, cyproterone acetate, nilutamide, or bicalutamide, or a pharmaceutically acceptable salt, crystal or enantiomeric form thereof, or a combination thereof, in a biodegradable ceramic carrier.

36. The kit according to claim 35, wherein the first component is a pharmaceutical composition for local administration in the prostate.

37. The kit according to claim 36, wherein the pharmaceutical composition comprises a ceramic carrier.

38. The method according to claim 13, wherein the active substance is flutamide.

39. The method according to claim 1, wherein the active substance is cyproterone acetate.

40. The method according to claim 1, wherein the active substance is nilutamide.

* * * * *

UNITED STATES PATENT AND TRADEMARK OFFICE
CERTIFICATE OF CORRECTION

| | | |
|---|---|---|
| PATENT NO. | : 8,936,809 B2 | Page 1 of 1 |
| APPLICATION NO. | : 11/910162 | |
| DATED | : January 20, 2015 | |
| INVENTOR(S) | : Lennernäs et al. | |

It is certified that error appears in the above-identified patent and that said Letters Patent is hereby corrected as shown below:

In the Claims,

Column 33
Line 16, "salt crystal" should read --salt, crystal--.

Column 33
Line 20, "one or more," should read --one or more--.

Column 34
Line 50, "obtained dining" should read --obtained during--.

Signed and Sealed this
Second Day of June, 2015

Michelle K. Lee
*Director of the United States Patent and Trademark Office*